US009850332B2

(12) United States Patent
Lue et al.

(10) Patent No.: US 9,850,332 B2
(45) Date of Patent: *Dec. 26, 2017

(54) PRODUCING POLYOLEFIN PRODUCTS WITH IMPROVED STIFFNESS, TOUGHNESS, AND PROCESSABILITY

(71) Applicant: Univation Technologies, LLC, Houston, TX (US)

(72) Inventors: Ching-Tai Lue, Sugar Land, TX (US); Francis C. Rix, League City, TX (US); Timothy M. Boller, Houston, TX (US); Garth R. Giesbrecht, The Woodlands, TX (US); Mark G. Goode, Hurricane, WV (US); Sun-Chueh Kao, Pearland, TX (US); Dongming Li, Houston, TX (US); R. Eric Pequeno, Baytown, TX (US); James M. Farley, League City, TX (US); Daniel P. Zilker, Jr., Charlestown, WV (US)

(73) Assignee: Univation Technologies, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/116,250

(22) PCT Filed: Feb. 10, 2015

(86) PCT No.: PCT/US2015/015119
§ 371 (c)(1),
(2) Date: Aug. 3, 2016

(87) PCT Pub. No.: WO2015/123164
PCT Pub. Date: Aug. 20, 2015

(65) Prior Publication Data
US 2016/0347888 A1  Dec. 1, 2016

Related U.S. Application Data

(60) Provisional application No. 61/938,466, filed on Feb. 11, 2014, provisional application No. 61/938,472, (Continued)

(51) Int. Cl.
*C08F 210/02* (2006.01)
*C08F 210/08* (2006.01)
(Continued)

(52) U.S. Cl.
CPC ............ *C08F 210/16* (2013.01); *C07F 17/00* (2013.01); *C08F 4/65904* (2013.01); *C08F 4/76* (2013.01);
(Continued)

(58) Field of Classification Search
None
See application file for complete search history.

(56) References Cited

U.S. PATENT DOCUMENTS 6,255,426 B1   7/2001   Lue et al.
6,943,227 B2   9/2005   Ishihama et al.
(Continued)

FOREIGN PATENT DOCUMENTS

CA   2780508   12/2013
JP   2003105029   4/2003
(Continued)

OTHER PUBLICATIONS

International Preliminary Report on Patentability for related PCT Application PCT/US2015/015119, dated Aug. 25, 2016 (12 pgs).
(Continued)

*Primary Examiner* — Richard A Huhn
(74) *Attorney, Agent, or Firm* — Brooks, Cameron & Huebsch, PLLC

(57) ABSTRACT

Polymers, and systems and methods for making and using the same are described herein. A polymer includes ethylene (Continued)

and at least one alpha olefin having from 4 to 20 carbon atoms. The polymer has a melt index ratio (MIR) greater than about 40. The polymer also has a value for Mw1/Mw2 of at least about 2.0, wherein Mw1/Mw2 is a ratio of a weight average molecular weight (Mw) for a first half of a temperature rising elution (TREF) curve from a cross-fractionation (CFC) analysis to an Mw for a second half of the TREF curve. The polymer also has a value for Tw1−Tw2 of less than about −15° C., wherein Tw1−Tw2 is a difference of a weight average elution temperature (Tw) for the first half of the TREF curve to a Tw for the second half of the TREF curve.

17 Claims, 8 Drawing Sheets

Related U.S. Application Data filed on Feb. 11, 2014, provisional application No. 61/981,291, filed on Apr. 18, 2014, provisional application No. 61/985,151, filed on Apr. 28, 2014, provisional application No. 62/032,383, filed on Aug. 1, 2014, provisional application No. 62/087,905, filed on Dec. 5, 2014, provisional application No. 62/088,196, filed on Dec. 5, 2014, provisional application No. 62/087,914, filed on Dec. 5, 2014, provisional application No. 62/087,911, filed on Dec. 5, 2014.

(51) Int. Cl.

| | | |
|---|---|---|
| *C08F 210/14* | (2006.01) | |
| *C08F 4/76* | (2006.01) | |
| *C08F 210/16* | (2006.01) | |
| *C08F 4/659* | (2006.01) | |
| *C07F 17/00* | (2006.01) | |
| *C08L 23/08* | (2006.01) | |
| *C08F 4/6592* | (2006.01) | |

(52) U.S. Cl.
CPC ........ *C08F 210/02* (2013.01); *C08F 4/65912* (2013.01); *C08F 4/65916* (2013.01); *C08F 4/65925* (2013.01); *C08F 4/65927* (2013.01); *C08F 210/08* (2013.01); *C08F 210/14* (2013.01); *C08F 2410/02* (2013.01); *C08F 2420/00* (2013.01); *C08F 2420/01* (2013.01); *C08F 2500/01* (2013.01); *C08F 2500/02* (2013.01); *C08F 2500/08* (2013.01); *C08F 2500/09* (2013.01); *C08F 2500/10* (2013.01); *C08F 2500/11* (2013.01); *C08F 2500/12* (2013.01); *C08F 2500/13* (2013.01); *C08F 2500/18* (2013.01); *C08F 2800/20* (2013.01); *C08L 23/0815* (2013.01)

(56) References Cited

U.S. PATENT DOCUMENTS

| | | | |
|---|---|---|---|
| 7,763,561 | B2 | 7/2010 | McDaniel et al. |
| 8,288,487 | B2 | 10/2012 | Yang et al. |
| 8,664,140 | B2 | 3/2014 | Schmitz et al. |
| 8,859,451 | B2 | 10/2014 | Mihan et al. |
| 8,932,975 | B2 | 1/2015 | Yang et al. |
| 8,999,875 | B2 | 4/2015 | Fantinel et al. |
| 9,346,896 | B2 | 5/2016 | McDaniel et al. |
| 2003/0008980 | A1 | 1/2003 | Mawson et al. |
| 2003/0096128 | A1 | 5/2003 | Farley et al. |
| 2009/0240010 | A1 | 9/2009 | McDaniel et al. |
| 2010/0076167 | A1 | 3/2010 | McDaniel et al. |
| 2010/0317904 | A1 | 12/2010 | Small et al. |
| 2011/0040041 | A1 | 2/2011 | Kolb et al. |
| 2012/0010375 | A1 | 1/2012 | Yang et al. |
| 2012/0059134 | A1 | 3/2012 | Yang et al. |

FOREIGN PATENT DOCUMENTS

| | | |
|---|---|---|
| JP | 2009126902 | 6/2009 |
| WO | 9504761 | 2/1995 |
| WO | 99/03897 | 1/1999 |
| WO | 0109200 | 2/2001 |
| WO | 2014074622 | 5/2014 |
| WO | 2014089671 | 6/2014 |

OTHER PUBLICATIONS

International Search Report & Written Opinion for related PCT Application PCT/US2015/015119, dated Jul. 23, 2015 (18 pgs).

400

PRODUCING POLYOLEFIN PRODUCTS WITH IMPROVED STIFFNESS, TOUGHNESS, AND PROCESSABILITY

RELATED APPLICATIONS

This application is a National Stage Application under 35 U.S.C. §371 of International Application Number PCT/US2015/015119, filed Feb. 10, 2015 and published as WO 2015/123164 on Aug. 20, 2015, which claims the benefit to the following U.S. Provisional Applications 61/938,466, filed Feb. 11, 2014; 61/938,472, filed Feb. 11, 2014; 61/981,291, filed Apr. 18, 2014; 61/985,151, filed Apr. 28, 2014; 62/032,383, filed Aug. 1, 2014; 62/087,905, filed Dec. 5, 2014; 62/088,196, filed Dec. 5, 2014; 62/087,914, filed Dec. 5, 2014; 62/087,911, filed Dec. 5, 2014; the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution as the reaction temperature is increased, for example, to increase production rates. Further, a single site catalyst will often incorporate comonomer among the molecules of the polyethylene copolymer at a relatively uniform rate. The molecular weight distribution (MWD) and the amount of comonomer incorporation can be used to determine a SCBD.

For an ethylene alpha-olefin copolymer, short chain branching (SCB) on a polymer chain is typically created through comonomer incorporation during polymerization. Short chain branch distribution (SCBD) refers to the distribution of short chain branches within a molecule or among different molecules that comprise the polyethylene polymer. When the amount of SCB varies among the polyethylene molecules, the resin is said to have a "broad" SCBD. When the amount of SCB is similar among the polyethylene molecules of different chain lengths, the SCBD is said to be "narrow".

SCBD is known to influence the properties of copolymers, for example, stiffness, toughness, extractable content, environmental stress crack resistance, and heat sealing, among other properties. SCBD of a polyolefin may be readily measured by methods known in the art, for example, Temperature Raising Elution Fractionation (TREF) or Crystallization Analysis Fractionation (CRYSTAF).

It is generally known in the art that a polyolefin's MWD and SCBD is largely dictated by the type of catalyst used and is often invariable for a given catalyst system. Ziegler-Natta catalysts and chromium based catalysts produce polymers with broad SCBD, whereas metallocene catalysts normally produce polymers with narrow SCBD. It has been long observed in the industry that there are trade-off paradigms among the different product attributes; most noticeably among stiffness, toughness, and processability (S/T/P). Since the introduction of metallocene in 1990s, some of such paradigms have been relaxed significantly with careful manipulations of molecular structure and composition in the product.

Polymers having a broad orthogonal composition distribution (BOCD) in which the comonomer is incorporated preferentially in the high molecular weight chains can lead to improved physical properties, for example, stiffness, toughness, processability, and environmental stress crack resistance (ESCR), among others. Because of the improved physical properties of polymers with orthogonal composition distributions needed for commercially desirable products, there exists a need for controlled techniques for forming polyethylene copolymers having a broad orthogonal composition distribution.

SUMMARY

An embodiment described herein provides a polymer that includes ethylene and at least one alpha olefin having from 4 to 20 carbon atoms. The polymer has a melt index ratio (MIR) greater than about 40. The polymer also has a value for Mw1/Mw2 of at least about 2.0, wherein Mw1/Mw2 is a ratio of a weight average molecular weight (Mw) for a first half of a temperature rising elution (TREF) curve from Cross-Fractionation (CFC) to an Mw for a second half of the TREF curve. The polymer also has a value for Tw1−Tw2 of less than about −15° C., wherein Tw1−Tw2 is a difference of a weight average elution temperature (Tw) for the first half of the TREF curve to a Tw for the second half of the TREF curve.

Another embodiment provides a polymer that includes ethylene and at least one alpha olefin having from 4 to 20 carbon atoms. The polymer has a density between about 0.915 and about 0.935, an average modulus of greater than about 30,000 psi, a dart impact strength of greater than about 100 g/mil, and a melt index ratio (MIR) greater than about 40. The polymer also lacks a negative inflection point in a van Gurp Palmen (vGP) plot at a frequency of between about 0.1 rad/s and 200 rad/s at 190° C.

Another embodiment provides a polymer that includes ethylene and at least one alpha olefin having from 4 to 20 carbon atoms. The polymer lacks a negative inflection point in a van Gurp Palmen (vGP) plot at a frequency of between about 0.1 rad/s and 300 rad/s at 190° C. The polymer also has a melt index ratio (MIR) greater than about 30 and a relationship between average modulus (M) and dart impact strength in g/mil (DIS) complying with the formula $$DIS \geq 0.8 \times [100 + e^{(11.71 - 0.000268 \times M + 2.183 \times 10^{-9} \times M^2)}].$$

DETAILED DESCRIPTION

Figure 1:
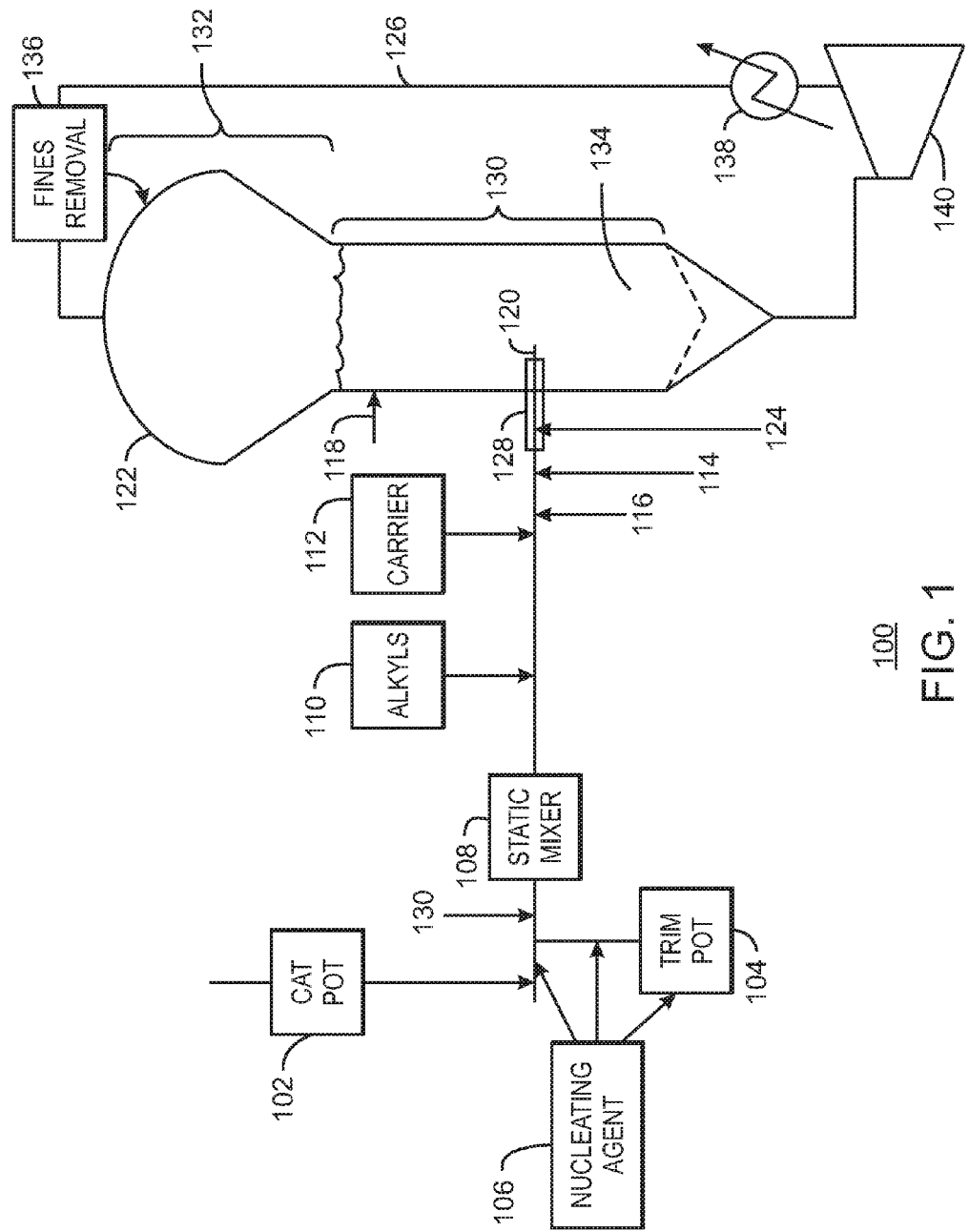
FIG. 1 is a schematic of a gas-phase reactor system, showing the addition of at least two catalysts, at least one of which is added as a trim catalyst.

It has been discovered that when a support is impregnated with multiple catalysts, new polymeric materials with improved balance of stiffness, toughness and processability can be achieved, e.g., by controlling the amounts and types of catalysts present on the support. As described in embodiments herein, appropriate selection of the catalysts and ratios may be used to adjust the molecular weight distribution (MWD), short chain branch distribution (SCBD), and long-chain branch distribution (LCBD) of the polymer, for example, to provide a polymer with a broad orthogonal composition distribution (BOCD). The MWD, SCBD, and LCBDs would be controlled by combining catalysts with the appropriate weight average molecular weight (Mw), comonomer incorporation, and long chain branching (LCB) formation under the conditions of the polymerization.

Employing multiple pre-catalysts that are co-supported on a single support mixed with an activator, such as a silica methylaluminoxane (SMAO), can provide a cost advantage by making the product in one reactor instead of multiple reactors. Further, using a single support also ensures intimate mixing of the polymers and offers improved operability relative to preparing a mixture of polymers of different Mw and density independently from multiple catalysts in a single reactor. As used herein, a pre-catalyst is a catalyst compound prior to exposure to activator.

As an example, for linear low-density polyethylene film (LLDPE) film applications, it would be desirable to prepare an ethylene hexene copolymer with a molecular weight of between about 90 Kg/mol and 110 Kg/mol, or about 100 Kg/mol and an average density of between about 0.9 and 0.925, or about 0.918 g/cm$^3$. The typical MWD for linear metallocene polymers is 2.0-3.5. Blend studies indicate it would be desirable to broaden this distribution by employing two catalysts that each provides different average molecular weights. The ratio of the Mw for the low molecular weight component and the high molecular weight component would be between 1:1 and 1:10, or about 1:2 and 1:5.

The density of a polyethylene copolymer provides an indication of the incorporation of comonomer into a polymer, with lower densities indicating higher incorporation. The difference in the densities of the low molecular weight (LMW) component and the high molecular weight (HMW) component would preferably be greater than about 0.02, or greater than about 0.04, with the HMW component having a lower density than the LMW component. For two polymers with Mw of 25 Kg/mol and 125 Kg/mol, the difference in density requires around a 4:1 difference in comonomer incorporation ability. It is also desirable to minimize the level of long chain branching (LCB) in the polymer as that provides strong orientation in film fabrication which imbalances MD/TD tear and reduces toughness.

These factors can be adjusted by controlling the MWD and SCBD, which, in turn, can be adjusted by changing the relative amount of the two pre-catalysts on the support. This may be adjusted during the formation of the pre-catalysts, for example, by supporting two catalysts on a single support. In some embodiments, the relative amounts of the pre-catalysts can be adjusted by adding one of the components to a catalyst mixture en-route to the reactor in a process termed "trim." Feedback of polymer property data can be used to control the amount of catalyst addition. Metallocenes (MCNs) are known to trim well with other catalysts.

Further, a variety of polymers with different MWD, SCBD, and LCBD may be prepared from a limited number of catalysts. To perform this function, the pre-catalysts should trim well onto activator supports. Two parameters that benefit this are solubility in alkane solvents and rapid supportation on the catalyst slurry en-route to the reactor. This favors the use of MCNs to achieve controlled MWD, SCBD, and LCBD. Techniques for selecting catalysts that can be used to generate targeted molecular weight compositions, including BOCD polymer systems, are disclosed herein.

Various catalyst systems and components may be used to generate the polymers and molecular weight compositions disclosed. These are discussed in the sections to follow. The first section discusses catalyst compounds that can be used in embodiments, including single site and metallocene catalysts, among others. The second section discusses generating catalyst slurrys that may be used for implementing the techniques described. The third section discusses supports that may be used. The fourth section discusses catalyst activators that may be used. The fifth section discusses the catalyst component solutions that may be used to add additional catalysts in trim systems. Gas phase polymerizations may use static control or continuity agents, which are discussed in the fifth section. A gas-phase polymerization reactor with a trim feed system is discussed in the sixth section. The use of the catalyst composition to control product properties is discussed in a sixth section and an exemplary polymerization process is discussed in the seventh section. Examples of the implementation of the procedures discussed in incorporated into an eighth section.

Catalyst Compounds

Metallocene Catalyst Compounds

Metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving groups bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring systems, at least a portion of which includes π-bonded systems, such as cycloalkadienyl ligands and heterocyclic analogues. The rings or ring systems typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligands are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$ Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one exemplary embodiment; and selected from the group consisting of Groups 3 through 10 atoms in a more particular exemplary embodiment, and selected from the group consisting of Sc, Ti, Zr, Hf, V, Nb, Ta, Mn, Re, Fe, Ru, Os, Co, Rh, Ir, and Ni in yet a more particular exemplary embodiment; and selected from the group consisting of Groups 4, 5, and 6 atoms in yet a more particular exemplary embodiment, and Ti, Zr, Hf atoms in yet a more particular exemplary embodiment, and Hf in yet a more particular exemplary embodiment. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the formula (I):

$$Cp^A Cp^B MX_n \qquad (I)$$

in which M is as described above; each X is chemically bonded to M; each Cp group is chemically bonded to M; and n is 0 or an integer from 1 to 4, and either 1 or 2 in a particular exemplary embodiment.

The ligands represented by $Cp^A$ and $Cp^B$ in formula (I) can be the same or different cyclopentadienyl ligands or ligands isolobal to cyclopentadienyl, either or both of which can contain heteroatoms and either or both of which can be substituted by a group R. In at least one specific embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) can be unsubstituted or substituted with any one or combination of substituent groups R. Non-limiting examples of substituent groups R as used in structure (I) as well as ring substituents in structures Va-d, discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof. More particular non-limiting examples of alkyl substituents R associated with formulas (I) through (Va-d) include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like. Other possible radicals include substituted alkyls and aryls such as, for example, fluoromethyl, fluroethyl, difluroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide, and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each X in the formula (I) above and for the formulas, or structures, (II) through (Va-d) below is independently selected from the group consisting of: any leaving group, in one exemplary embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_8$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, in a more particular exemplary embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls, in yet a more particular exemplary embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls, in yet a more particular exemplary embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment; and fluoride, in yet a more particular exemplary embodiment.

Other non-limiting examples of X groups include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more Xs form a part of a fused ring or ring system. In at least one specific embodiment, X can be a leaving group selected from the group consisting of chloride ions, bromide ions, $C_1$ to $C_{10}$ alkyls, and $C_2$ to $C_{12}$ alkenyls, carboxylates, acetylacetonates, and alkoxides.

The metallocene catalyst compound includes those of formula (I) where $Cp^A$ and $Cp^B$ are bridged to each other by at least one bridging group, (A), such that the structure is represented by formula (II):

$$Cp^A(A)Cp^BMX_n \qquad (II)$$

These bridged compounds represented by formula (II) are known as "bridged metallocenes." The elements $Cp^A$, $Cp^B$, M, X and n in formula (II) are as defined above for formula (I); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be $C_1$ to $C_{12}$ alkyl or aryl substituted to satisfy neutral valency. In at least one specific embodiment, the bridging group (A) can also include substituent groups R as defined above (for formula (I)) including halogen radicals and iron. In at least one specific embodiment, the bridging group (A) can be represented by $C_1$ to $C_6$ alkylenes, substituted $C_1$ to $C_6$ alkylenes, oxygen, sulfur, $R'_2C=$, $R'_2Si=$, $=Si(R')_2Si(R'_2)=$, $R'_2Ge=$, and $R'P=$, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of formula (II) includes two or more bridging groups (A). In one or more embodiments, (A) can be a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties where the Si atom is replaced by a Ge or a C atom; as well as dimethylsilyl, diethylsilyl, dimethylgermyl and diethylgermyl.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, Cl). The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands $Cp^A$ and $Cp^B$ of formula (I) and (II) can be different from each other. The ligands $Cp^A$ and $Cp^B$ of formula (I) and (II) can be the same. The metallocene catalyst compound can include bridged mono-ligand metallocene compounds (e.g., mono cyclopentadienyl catalyst components).

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

The amount of the transition metal component of the one or more metallocene catalyst compounds in the catalyst system can range from a low of about 0.2 wt. %, about 3 wt. %, about 0.5 wt. %, or about 0.7 wt. % to a high of about 1 wt. %, about 2 wt. %, about 2.5 wt. %, about 3 wt. %, about 3.5 wt. %, or about 4 wt. %, based on the total weight of the catalyst system.

The "metallocene catalyst compound" can include any combination of any "embodiment" discussed and described herein. Further, other single site catalysts, which may technically no be metallocene catalysts, can be referred to by this term. For example, the metallocene catalyst compound can include, but is not limited to, bis(n-propylcyclopentadienyl) hafnium $(CH_3)_2$, bis(n-propylcyclopentadienyl) hafnium $F_2$, bis(n-propylcyclopentadienyl) hafnium $Cl_2$, bis(n-butyl, methyl cyclopentadienyl) zirconium $Cl_2$, or $[(2,3,4,5,6\text{-}Me_5C_6N)CH_2CH_2]_2NHZrBn_2$, where Bn is a benzyl group, or any combination thereof.

Other metallocene catalyst compounds that may be used are supported constrained geometry catalysts (sCGC) that include (a) an ionic complex, (b) a transition metal compound, (c) an organometal compound, and (d) a support material. In some embodiments, the sCGC catalyst may include a borate ion. The borate anion is represented by the formula $[BQ_{4-z'}(G_q(T\text{-}H)_r)_{z'}]^{d-}$, wherein: B is boron in a valence state of 3; Q is selected from the group consisting of hydride, dihydrocarbylamido, halide, hydrocarbyloxide, hydrocarbyl, and substituted-hydrocarbyl radicals; z' is an integer in a range from 1 to 4; G is a polyvalent hydrocarbon radical having r+1 valencies bonded to M' and r groups (T--H); q is an integer, 0 or 1; the group (T--H) is a radical wherein T includes O, S, NR, or PR, the O, S, N or P atom of which is bonded to hydrogen atom H, wherein R is a hydrocarbyl radical, a trihydrocarbylsilyl radical, a trihydrocarbyl germyl radical or hydrogen; r is an integer from 1 to 3; and d is 1. Alternatively the borate ion may be representative by the formula $[BQ_{4-z'}(G_q(T\text{-}M^\circ R^C_{x-1} X^a_y)_r)_{z'}]^{d-}$, wherein: B is boron in a valence state of 3; Q is selected from the group consisting of hydride, dihydrocarbylamido, halide, hydrocarbyloxide, hydrocarbyl, and substituted-hydrocarbyl radicals; z' is an integer in a range from 1 to 4; G is a polyvalent hydrocarbon radical having r+1 valencies bonded to B and r groups $(T\text{-}M^\circ R^C_{x-1} X^a_y)$; q is an integer, 0 or 1; the group $(T\text{-}M^\circ R^C_{x-1} X^a_y)$ is a radical wherein T includes O, S, NR, or PR, the O, S, N or P atom of which is bonded to $M^\circ$, wherein R is a hydrocarbyl radical, a trihydrocarbylsilyl radical, a trihydrocarbyl germyl radical or hydrogen; $M^\circ$ is a metal or metalloid selected from Groups 1-14 of the Periodic Table of the Elements, $R^C$ independently each occurrence is hydrogen or a group having from 1 to 80 nonhydrogen atoms which is hydrocarbyl, hydrocarbylsilyl, or hydrocarbylsilylhydrocarbyl; $X^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl)amino, hydrocarbyloxy or halide; x is a nonzero integer which may range from 1 to an integer equal to the valence of $M^\circ$; y is zero or a nonzero integer which may range from 1 to an integer equal to 1 less than the valence of $M^\circ$; and x+y equals the valence of $M^\circ$; r is an integer from 1 to 3; and d is 1. In some embodiments, the borate ion may be of the above described formulas where z' is 1 or 2, q is 1, and r is 1.

The catalyst system can include other single site catalysts such as Group 15-containing catalysts. The catalyst system can include one or more second catalysts in addition to the single site catalyst compound such as chromium-based catalysts, Ziegler-Natta catalysts, one or more additional single-site catalysts such as metallocenes or Group 15-containing catalysts, bimetallic catalysts, and mixed catalysts. The catalyst system can also include $AlCl_3$, cobalt, iron, palladium, or any combination thereof.

Illustrative but non-limiting examples of metallocene catalyst compounds include: bis(cyclopentadienyl) titanium dimethyl, bis(cyclopentadienyl) titanium diphenyl, bis(cyclopentadienyl) zirconium dimethyl, bis(cyclopentadienyl) zirconium diphenyl, bis(cyclopentadienyl) hafnium dimethyl or diphenyl, bis(propylcyclopentadienyl) hafnium, dimethyl, bis(cyclopentadienyl) titanium di-neopentyl, bis(cyclopentadienyl) zirconium di-neopentyl, bis(indenyl) zirconium dimethyl (rac and mes), bis(cyclopentadienyl) titanium dibenzyl, bis(cyclopentadienyl) zirconium dibenzyl, bis(cyclopentadienyl) vanadium dimethyl, bis(cyclopentadienyl) titanium methyl chloride, (pentamethylcyclopentadienyl) (1-methylindenyl) zirconium dimethyl, (tetramethylcyclopentadienyl) (1,3-dimethylindenyl) zirconium dimethyl, bis(cyclopentadienyl) titanium ethyl chloride, bis (cyclopentadienyl) titanium phenyl chloride, bis(cyclopentadienyl) zirconium methyl chloride, bis(cyclopentadienyl) zirconium ethyl chloride, bis(cyclopentadienyl) zirconium phenyl chloride, bis(cyclopentadienyl) titanium methyl bromide, cyclopentadienyl titanium trimethyl, cyclopentadienyl zirconium triphenyl, cyclopentadienyl zirconium trineopentyl, cyclopentadienyl zirconium trimethyl, cyclopentadienyl hafnium triphenyl, cyclopentadienyl hafnium trineopentyl, cyclopentadienyl hafnium trimethyl, pentamethylcyclopentadienyl titanium trichloride, pentaethylcyclopentadienyl titanium trichloride, bis(indenyl) titanium diphenyl or dichloride, bis(methylcyclopentadienyl) titanium diphenyl or dihalide, bis(1,2-dimethylcyclopentadienyl) titanium diphenyl or dichloride, bis(1,2-diethylcyclopentadienyl) titanium diphenyl or dichloride, bis(pentamethyl cyclopentadienyl) titanium diphenyl or dichloride; dimethyl silyldicyclopentadienyl titanium diphenyl or dichloride, methyl phosphine dicyclopentadienyl titanium diphenyl or dichloride, methylenedicyclopentadienyl titanium diphenyl or dichloride, isopropyl (cyclopentadienyl) (fluorenyl) zirconium dichloride, isopropyl(cyclopentadienyl) (octahydrofluorenyl) zirconium dichloride, diisopropylmethylene (cyclopentadienyl) (fluorenyl) zirconium dichloride, diisobutylmethylene (cyclopentadienyl) (fluorenyl) zirconium dichloride, ditertbutylmethylene (cyclopentadienyl) (fluorenyl) zirconium dichloride, cyclohexylidene (cyclopentadienyl) (fluorenyl) zirconium dichloride, diisopropylmethylene (2,5-dimetycyclopentadienyl) (fluorenyl) zirconium dichloride, isopropyl (cyclopentadienyl) (fluorenyl) hafnium dichloride, diphenylmethylene (cyclopentadienyl) (fluorenyl) hafnium dichloride, diisopropylmethylene (cyclopentadienyl) (fluorenyl) hafnium dichloride, diisobutylmethylene (cyclopentadienyl) (fluorenyl)hafnium dichloride, ditertbutylmethylene (cyclopentadienyl) (fluorenyl) hafnium dichloride, cyclohexylindene (cyclopentadienyl) (fluorenyl) hafnium dichloride, diisopropylmethylene (2,5-dimethylcyclopentadienyl) (fluorenyl) hafnium dichloride, isopropyl (cyclopentadienyl) (fluorenyl) titanium dichloride, diphenylmethylene (cyclopentadienyl) (fluorenyl) titanium dichloride, diisopropylmethylene (cyclopentadienyl) (fluorenyl) titanium dichloride, diisobutylmethylene (cyclopentadienyl) (fluorenyl) titanium dichloride, ditertbutylmethylene (cyclopentadienyl) (fluorenyl) titanium dichloride, cyclohexylidene (cyclopentadienyl) (fluorenyl)titanium dichloride, diisopropylmethylene (2,5-dimethylcyclopentadienyl fluorenyl) titanium dichloride, racemic-ethylene bis (1-indenyl) zirconium (W) dichloride, racemic-ethylene bis (4,5,6,7-tetrahydro-1-indenyl) zirconium (IV) dichloride, racemic-dimethylsilyl bis(1-indenyl) zirconium (IV) dichloride, racemic-dimethylsilyl bis(4,5,6,7-tetrahydro-1-indenyl) zirconium (IV) dichloride, racemic-1,1,2,2-tetramethylsilanylene bis(1-indenyl) zirconium (IV) dichloride, racemic-1,1,2,2-tetramethylsilanylene bis(4,5,6,7-tetrahydro-1-indenyl) zirconium (IV) dichloride, ethylidene (1-indenyl tetramethylcyclopentadienyl) zirconium (IV) dichloride, racemic-dimethylsilyl bis(2-methyl-4-t-butyl-1-cyclopentadienyl)zirconium (IV) dichloride, racemic-ethylene bis(1-indenyl)hafnium (IV) dichloride, racemic-ethylene bis(4,5,6,7-tetrahydro-1-indenyl) hafnium (IV) dichloride, racemic-dimethylsilyl bis(1-indenyl) hafnium (IV) dichloride, racemic-dimethylsilyl bis(4,5,6,7-tetrahydro-1-indenyl) hafnium (IV) dichloride, racemic-1,1,2,2-tetramethylsilanylene bis(1-indenyl) hafnium (IV) dichloride, racemic-1,1,2,2-tetramethylsilanylene bis(4,5,6,7-tetrahydro-1-indenyl) hafnium (IV), dichloride, ethylidene (1-indenyl-2,3,4,5-tetramethyl-1-cyclopentadienyl) hafnium (IV) dichloride, racemic-ethylene bis(1-indenyl) titanium (IV) dichloride, racemic-ethylene bis(4,5,6,7-tetrahydro-1-indenyl) titanium (IV) dichloride, racemic-dimethylsilyl bis (1-indenyl) titanium (IV) dichloride, racemic-dimethylsilyl bis(4,5,6,7-tetrahydro-1-indenyl) titanium (IV) dichloride, racemic-1,1,2,2-tetramethylsilanylene bis(1-indenyl) titanium (IV) dichloride racemic-1,1,2,2-tetramethylsilanylene bis(4,5,6,7-tetrahydro-1-indenyl) titanium (IV) dichloride, and ethylidene (1-indenyl-2,3,4,5-tetramethyl-1-cyclopentadienyl) titanium (IV) dichloride.

Other metallocene catalyst compounds that may be used in embodiments are diphenylmethylene (cyclopentadienyl)(fluorenyl) zirconium dichloride, racemic-dimethylsilyl bis(2-methyl-1-indenyl) zirconium (IV) dichloride, racemic-dimethylsilyl bis(2-methyl-4-(1-naphthyl-1-indenyl) zirconium (IV) dichloride, and racemic-dimethylsilyl bis(2-methyl-4-phenyl-1-indenyl) zirconium (IV) dichloride. Further metallocene catalyst compounds include, indenyl zirconium tris(diethylcarbamate), indenyl zirconium tris(pivalate), indenyl zirconium tris(p-toluate), indenyl zirconium tris(benzoate), (1-methylindenyl)zirconium tris(pivalate), (2-methylindenyl)zirconium tris(diethylcarbamate), (methylcyclopentadienyl)zirconium tris(pivalate), cyclopentadienyl tris(pivalate), and (pentamethylcyclopentadienyl)zirconium tris(benzoate).

Examples of structures of MCN compounds that may be used in embodiments include the hafnium compound shown as formula (III), the zirconium compounds shown as formulas (IV-A-D), and bridged zirconium compounds, shown as formulas (V-A and B):

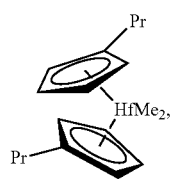
(III)

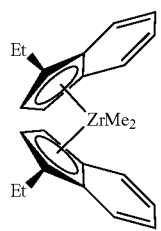
(IV-A)

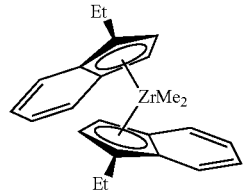
(IV-B)

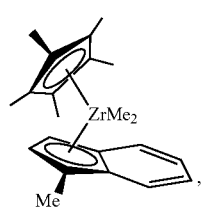
(IV-C)

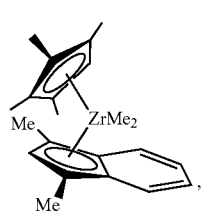
(IV-D)

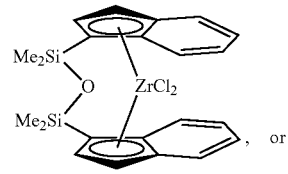
(V-A)

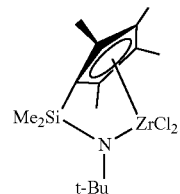
(V-B)

Although these compounds are shown with methyl- and chloro-groups attached to the central metal, it can be understood that these groups may be different without changing the catalyst involved. For example, each of these substituents may independently be a methyl group (Me), a chloro group (Cl), a fluoro group (F), or any number of other groups, including organic groups, or heteroatom groups. Further, these substituents will change during the reaction, as a pre-catalyst is converted to the active catalyst for the reaction.

Group 15 Atom and Metal-Containing Catalyst Compounds

The catalyst system can include one or more Group 15 metal-containing catalyst compounds. The Group 15 metal-containing compound generally includes a Group 3 to 14 metal atom, a Group 3 to 7, or a Group 4 to 6 metal atom. In many embodiments, the Group 15 metal-containing compound includes a Group 4 metal atom bound to at least one leaving group and also bound to at least two Group 15 atoms, at least one of which is also bound to a Group 15 or 16 atom through another group.

In one or more embodiments, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and can optionally be bound to hydrogen, a halogen, a heteroatom or a hydrocarbyl group, or a heteroatom containing group.

The Group 15-containing metal compounds can be described more particularly with formulas (VI) or (VII):

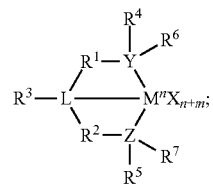
(VI)

-continued

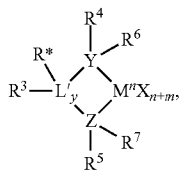

(VII)

in which M is a Group 3 to 12 transition metal or a Group 13 or 14 main group metal or a Group 4, 5, or 6 metal. In many embodiments, M is a Group 4 metal, such as zirconium, titanium or hafnium. Each X is independently a leaving group, such as an anionic leaving group. The leaving group may include a hydrogen, a hydrocarbyl group, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or the YZL' ligand, and is 0, −1, −2 or −3 in various embodiments. In many embodiments, m is −2. L is a Group 15 or 16 element, such as nitrogen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. $R^1$ and $R^2$ are, independently, a $C_1$ to $C_{20}$ hydrocarbon group, a heteroatom containing group having up to twenty carbon atoms, silicon, germanium, tin, lead, or phosphorus. In many embodiments, $R^1$ and $R^2$ are a $C_2$ to $C_{20}$ alkyl, aryl, or aralkyl group, such as a linear, branched, or cyclic $C_2$ to $C_{20}$ alkyl group, or a $C_2$ to $C_6$ hydrocarbon group. $R^1$ and $R^2$ may also be interconnected to each other. $R^3$ may be absent or may be a hydrocarbon group, a hydrogen, a halogen, a heteroatom containing group. In many embodiments, $R^3$ is absent or a hydrogen, or a linear, cyclic or branched alkyl group having 1 to 20 carbon atoms. $R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, often having up to 20 carbon atoms. In many embodiments, $R^4$ and $R^5$ have between 3 and 10 carbon atoms, or are a $C_1$ to $C_{20}$ hydrocarbon group, a $C_1$ to $C_{20}$ aryl group or a $C_1$ to $C_{20}$ aralkyl group, or a heteroatom containing group. $R^4$ and $R^5$ may be interconnected to each other. $R^6$ and $R^7$ are independently absent, hydrogen, an alkyl group, halogen, heteroatom, or a hydrocarbyl group, such as a linear, cyclic, or branched alkyl group having 1 to 20 carbon atoms. In many embodiments, $R^6$ and $R^7$ are absent. $R^*$ may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, $R^4$ and $R^5$ are independently a group represented by the following formula (VIII).

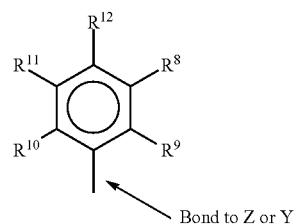

(VIII)

When $R^4$ and $R^5$ are as formula VII, $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by the following formula (IX).

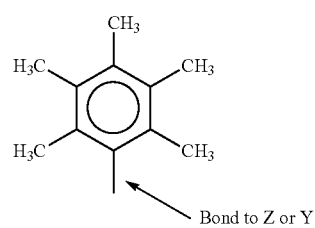

(IX)

When $R^4$ and $R^5$ follow formula IX, M is a Group 4 metal, such as zirconium, titanium, or hafnium. In many embodiments, M is zirconium. Each of L, Y, and Z may be a nitrogen. Each of $R^1$ and $R^2$ may be —$CH_2$—$CH_2$—. $R^3$ may be hydrogen, and $R^6$ and $R^7$ may be absent.

The Group 15 metal-containing catalyst compound can be represented by the following formula (X).

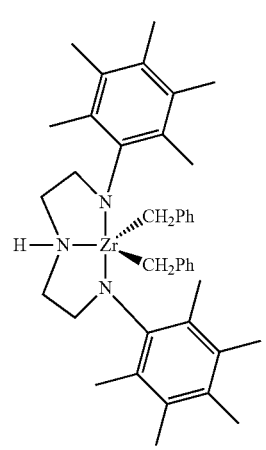

(X)

In formula X, Ph represents phenyl.

Slurry Catalyst

The catalyst system may include a catalyst component in a slurry, which may have an initial catalyst compound, and an added solution catalyst component that is added to the slurry. The initial catalyst component slurry may have no catalysts. In this case, two or more solution catalysts may be added to the slurry to cause each to be supported.

Any number of combinations of catalyst components may be used in embodiments. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and two catalyst compounds. In another embodiment the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator to metal in the catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

Support

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand. The single site catalyst compounds of the slurry can be spray dried. The support used with the single site catalyst compound can be functionalized.

The support can be or include one or more inorganic oxides, for example, of Group 2, 3, 4, 5, 13, or 14 elements. The inorganic oxide can include, but is not limited to, silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include silica, alumina, or a combination thereof. In one embodiment described herein, the support is silica. In another embodiment described herein, the support is silica-alumina.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalysts supports comprising silica gels with activators, such as methylaluminoxanes (MAOs), are used in the trim systems described, since these supports may function better for co-supporting solution carried catalysts.

Activator

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound/component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as tri (n-butyl)ammonium tetrakis(pentafluorophenyl) boron, a trisperfluorophenyl boron, a trisperfluoronaphthyl boron, or any combinations thereof.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes.

In one or more embodiments, a visually clear MAO can be used. For example, a cloudy or gelled aluminoxane can be filtered to produce a clear aluminoxane or clear aluminoxane can be decanted from a cloudy aluminoxane solution. In another embodiment, a cloudy and/or gelled aluminoxane can be used. Another aluminoxane can include a modified methyl aluminoxane ("MMAO") type 3A (commercially available from Akzo Chemicals, Inc. under the trade name Modified Methylaluminoxane type 3A). A suitable source of MAO can be a solution having from about 1 wt. % to about a 50 wt. % MAO, for example. Commercially available MAO solutions can include the 10 wt. % and 30 wt. % MAO solutions available from Albemarle Corporation, of Baton Rouge, La.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Catalyst Component Solution

The catalyst component solution may include only a catalyst compound or may include an activator in addition to the catalyst compound. The catalyst solution used in the trim process can be prepared by dissolving the catalyst compound and optional activators in a liquid solvent. The liquid solvent may be an alkane, such as a $C_5$ to $C_{30}$ alkane, or a $C_5$ to $C_{10}$ alkane. Cyclic alkanes such as cyclohexane and aromatic compounds such as toluene may also be used. In addition, mineral oil may be used as a solvent. The solution employed should be liquid under the conditions of polymerization and relatively inert. In one embodiment, the liquid utilized in the catalyst compound solution is different from the diluent used in the catalyst component slurry. In another embodiment, the liquid utilized in the catalyst compound solution is the same as the diluent used in the catalyst component solution.

If the catalyst solution includes both activator and catalyst compound, the ratio of metal in the activator to metal in the catalyst compound in the solution may be 1000:1 to 0.5:1, 300:1 to 1:1, or 150:1 to 1:1. In various embodiments, the activator and catalyst compound are present in the solution at up to about 90 wt. %, at up to about 50 wt. %, at up to about 20 wt. %, preferably at up to about 10 wt. %, at up to about 5 wt. %, at less than 1 wt. %, or between 100 ppm and 1 wt. %, based upon the weight of the solvent and the activator or catalyst compound.

The catalyst component solution can comprise any one of the soluble catalyst compounds described in the catalyst section herein. As the catalyst is dissolved in the solution, a higher solubility is desirable. Accordingly, the catalyst compound in the catalyst component solution may often include a metallocene, which may have higher solubility than other catalysts.

In the polymerization process, described below, any of the above described catalyst component containing solutions may be combined with any of the catalyst component containing slurry/slurries described above. In addition, more than one catalyst component solution may be utilized.

Continuity Additive/Static Control Agent

In gas-phase polyethylene production processes, it may be desirable to use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

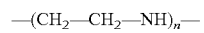

in which n may be from about 10 to about 10,000. The polyethyleneimines may be linear, branched, or hyperbranched (e.g., forming dendritic or arborescent polymer structures). They can be a homopolymer or copolymer of ethyleneimine or mixtures thereof (referred to as polyethyleneimines hereafter). Although linear polymers represented by the chemical formula —[$CH_2$—$CH_2$—NH]— may be used as the polyethyleneimine, materials having primary, secondary, and tertiary branches can also be used. Commercial polyethyleneimine can be a compound having branches of the ethyleneimine polymer.

Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil, e.g., in the commercially available product Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %.

The continuity additives or static control agents may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Gas Phase Polymerization Reactor

FIG. 1 is a schematic of a gas-phase reactor system 100, showing the addition of at least two catalysts, at least one of which is added as a trim catalyst. The catalyst component slurry, preferably a mineral oil slurry including at least one support and at least one activator, at least one supported activator, and optional catalyst compounds may be placed in a vessel or catalyst pot (cat pot) 102. In one embodiment, the cat pot 102 is an agitated holding tank designed to keep the solids concentration homogenous. A catalyst component solution, prepared by mixing a solvent and at least one catalyst compound and/or activator, is placed in another vessel, which can be termed a trim pot 104. The catalyst component slurry can then be combined in-line with the catalyst component solution to form a final catalyst composition. A nucleating agent 106, such as silica, alumina, fumed silica or any other particulate matter may be added to the slurry and/or the solution in-line or in the vessels 102 or 104. Similarly, additional activators or catalyst compounds may be added in-line. For example, a second catalyst slurry that includes a different catalyst may be introduced from a second cat pot. The two catalyst slurries may be used as the catalyst system with or without the addition of a solution catalyst from the trim pot.

The catalyst component slurry and solution can be mixed in-line. For example, the solution and slurry may be mixed by utilizing a static mixer 108 or an agitating vessel (not shown). The mixing of the catalyst component slurry and the catalyst component solution should be long enough to allow the catalyst compound in the catalyst component solution to disperse in the catalyst component slurry such that the catalyst component, originally in the solution, migrates to the supported activator originally present in the slurry. The combination forms a uniform dispersion of catalyst compounds on the supported activator forming the catalyst composition. The length of time that the slurry and the solution are contacted is typically up to about 120 minutes, such as about 1 to about 60 minutes, about 5 to about 40 minutes, or about 10 to about 30 minutes.

When combining the catalysts, the activator and the optional support or additional co-catalysts, in the hydrocarbon solvents immediately prior to a polymerization reactor it is desirable that the combination yield a new polymerization catalyst in less than 1 h, less than 30 min, or less than 15 min. Shorter times are more effective, as the new catalyst is ready before being introduces into the reactor, providing the potential for faster flow rates.

In another embodiment, an aluminum alkyl, an ethoxylated aluminum alkyl, an aluminoxane, an anti-static agent or a borate activator, such as a $C_1$ to $C_{15}$ alkyl aluminum (for example tri-isobutyl aluminum, trimethyl aluminum or the like), a $C_1$ to $C_{15}$ ethoxylated alkyl aluminum or methyl aluminoxane, ethyl aluminoxane, isobutylaluminoxane, modified aluminoxane or the like are added to the mixture of the slurry and the solution in line. The alkyls, antistatic agents, borate activators and/or aluminoxanes may be added from an alkyl vessel 110 directly to the combination of the solution and the slurry, or may be added via an additional alkane (such as isopentane, hexane, heptane, and or octane) carrier stream, for example, from a hydrocarbon vessel 112. The additional alkyls, antistatic agents, borate activators and/or aluminoxanes may be present at up to about 500 ppm, at about 1 to about 300 ppm, at 10 to about 300 ppm, or at about 10 to about 100 ppm. Carrier streams that may be used include isopentane and or hexane, among others. The carrier may be added to the mixture of the slurry and the solution, typically at a rate of about 0.5 to about 60 lbs/hr (27 kg/hr). Likewise a carrier gas 114, such as nitrogen, argon, ethane, propane and the like, may be added in-line to the mixture of the slurry and the solution. Typically the carrier gas may be added at the rate of about 1 to about 100 lb/hr (0.4 to 45 kg/hr), or about 1 to about 50 lb/hr (5 to 23 kg/hr), or about 1 to about 25 lb/hr (0.4 to 11 kg/hr).

In another embodiment, a liquid carrier stream is introduced into the combination of the solution and slurry that is moving in a downward direction. The mixture of the solution, the slurry and the liquid carrier stream may pass through a mixer or length of tube for mixing before being contacted with a gaseous carrier stream.

Similarly, a comonomer 116, such as 1-butene, 1-hexene, another alpha-olefin or diolefin, may be added in-line to the mixture of the slurry and the solution. The slurry/solution mixture is then passed through an injection tube 120 to a reactor 122. In some embodiments, the injection tube may aerosolize the slurry/solution mixture. Any number of suitable tubing sizes and configurations may be used to aerosolize and/or inject the slurry/solution mixture.

In one embodiment, a gas stream 124, such as cycle gas, or re-cycle gas 126, monomer, nitrogen, or other materials is introduced into a support tube 128 that surrounds the injection tube 120. To assist in proper formation of particles in the reactor 122, a nucleating agent 118, such as fumed silica, can be added directly into the reactor 122.

When a metallocene catalyst or other similar catalyst is used in the gas phase reactor, oxygen or fluorobenzene can be added to the reactor 122 directly or to the gas stream 126 to control the polymerization rate. Thus, when a metallocene catalyst (which is sensitive to oxygen or fluorobenzene) is used in combination with another catalyst (that is not sensitive to oxygen) in a gas phase reactor, oxygen can be used to modify the metallocene polymerization rate relative to the polymerization rate of the other catalyst. An example of such a catalyst combination is bis(n-propyl cyclopentadienyl)zirconium dichloride and $[(2,4,6-Me_3C_6H_2)NCH_2CH_2]_2NHZrBn_2$, where Me is methyl or bis(indenyl) zirconium dichloride and $[(2,4,6-Me_3C_6H_2)NCH_2CH_2]_2NHHfBn_2$, where Me is methyl. For example, if the oxygen concentration in the nitrogen feed is altered from 0.1 ppm to 0.5 ppm, significantly less polymer from the bisindenyl $ZrCl_2$ will be produced and the relative amount of polymer produced from the $[(2,4,6-Me_3C_6H_2)NCH_2CH_2]_2NHHfBn_2$ is increased. Water or carbon dioxide may be added to gas phase polymerization reactors, for example, for similar purposes. In one embodiment, the contact temperature of the slurry and the solution is in the range of from 0° C. to about 80° C., from about 0° C. to about 60° C., from about 10° C., to about 50° C., and from about 20° C. to about 40° C.

The example above is not limiting, as additional solutions and slurries may be included. For example, a slurry can be combined with two or more solutions having the same or different catalyst compounds and or activators. Likewise, the solution may be combined with two or more slurries each having the same or different supports, and the same or different catalyst compounds and or activators. Similarly, two or more slurries combined with two or more solutions, preferably in-line, where the slurries each comprise the same or different supports and may comprise the same or different catalyst compounds and or activators and the solutions comprise the same or different catalyst compounds and or activators. For example, the slurry may contain a supported activator and two different catalyst compounds, and two solutions, each containing one of the catalysts in the slurry, are each independently combined, in-line, with the slurry.

Use of Catalyst Composition to Control Product Properties

The properties of the product polymer may be controlled by adjusting the timing, temperature, concentrations, and sequence of the mixing of the solution, the slurry and any optional added materials (nucleating agents, catalyst compounds, activators, etc) described above. The MWD, SCBD, relative amount of polymer produced by each catalyst, and other properties of the polymer produced may also be changed by manipulating process parameters. Any number of process parameters may be adjusted, including manipulating hydrogen concentration in the polymerization system, changing the amount of the first catalyst in the polymerization system, or changing the amount of the second catalyst in the polymerization system, among others. Other process parameters that can be adjusted include changing the relative ratio of the catalyst in the polymerization process (and optionally adjusting their individual feed rates to maintain a steady or constant polymer production rate). The concentrations of reactants in the reactor 122 can be adjusted by changing the amount of liquid or gas that is withdrawn or purged from the process, changing the amount and/or composition of a recovered liquid and/or recovered gas returned to the polymerization process, wherein the recovered liquid or recovered gas can be recovered from polymer discharged from the polymerization process. Further parameters that can be adjusted include changing the polymerization temperature, changing the ethylene partial pressure in the polymerization process, changing the ethylene to comonomer ratio in the polymerization process, or changing the activator to transition metal ratio in the activation sequence, among others. Time dependent parameters may be adjusted, such as changing the relative feed rates of the slurry or solution, changing the mixing time, the temperature and or degree of mixing of the slurry and the solution in-line, adding different types of activator compounds to the polymerization process, and adding oxygen or fluorobenzene or other catalyst poison to the polymerization process. Any combinations of these adjustments may be used to control the properties of the final polymer product.

In one embodiment, the SCBD of the polymer product is measured at regular intervals and one of the above process parameters, such as temperature, catalyst compound feed rate, the ratio of the two or more catalysts to each other, the ratio of comonomer to monomer, the monomer partial pressure, and or hydrogen concentration, is altered to bring the composition to the desired level, if necessary. The SCBD may be performed by temperature rising elution fractionation (TREF), or similar techniques. As discussed in the examples, TREF can measure SCBD as a function of elution temperature. A combination of techniques may be used, such as measuring a molecular weight distribution of a number of the eluted fractions by gel permeation chromatography (GPC), as described below.

In one embodiment, a polymer product property is measured in-line and in response the ratio of the catalysts being combined is altered. In one embodiment, the molar ratio of the catalyst compound in the catalyst component slurry to the catalyst compound in the catalyst component solution, after the slurry and solution have been mixed to form the final catalyst composition, is 500:1 to 1:500, or 100:1 to 1:100, or 50:1 to 1:50 or 10:1 to 1:10, or 5:1 to 1:5. In another embodiment, the molar ratio of a Group 15 catalyst compound in the slurry to a ligand metallocene catalyst compound in the solution, after the slurry and solution have been mixed to form the catalyst composition, is 500:1, 100:1, 50:1, 10:1, 5:1, 1:5, 1:10, 1:100, or 1:500. The product property measured can include the dynamic shear viscosity, flow index, melt index, density, MWD, comonomer content, SCBD, and combinations thereof. The polyethylene polymers described herein can be uni-modal or multi-modal on its MWD and/or SCBD curves by e.g., GPC and TREF, respectively. In another embodiment, when the ratio of the catalyst compounds is altered, the introduction rate of the catalyst composition to the reactor, or other process parameters, is altered to maintain a desired production rate.

While not wishing to be bound by or limited to any theory, the inventors believe that the processes described herein immobilize the solution catalyst compound in and on a support, preferably a supported activator. The in-line immobilization techniques described herein preferably result in a supported catalyst system that when introduced to the reactor provides for suitable polymer properties, with appropriate particle morphology, bulk density, or higher catalyst activities and without the need for additional equipment in order to introduce catalyst compound solution into a reactor, particularly a gas phase or slurry phase reactor.

Polymerization Process

The catalyst system can be used to polymerize one or more olefins to provide one or more polymer products therefrom. Any suitable polymerization process can be used, including, but not limited to, high pressure, solution, slurry, and/or gas phase polymerization processes. In embodiments that use other techniques besides gas phase polymerization, modifications to a catalyst addition system that are similar to those discussed with respect to FIG. 1 can be used. For example, a trim system may be used to feed catalyst to a loop slurry reactor for polyethylene copolymer production.

The terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, at least 95 wt. % ethylene-derived units, or 100 wt. % ethylene-derived units. The polyethylene polymers described herein are generally copolymers, but may also include terpolymers, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like.

Referring again to FIG. 1, the fluidized bed reactor 122 can include a reaction zone 130 and a velocity reduction zone 132. The reaction zone 130 can include a bed 134 that includes growing polymer particles, formed polymer particles and a minor amount of catalyst particles fluidized by the continuous flow of the gaseous monomer and diluent to remove heat of polymerization through the reaction zone. Optionally, some of the re-circulated gases 124 can be cooled and compressed to form liquids that increase the heat removal capacity of the circulating gas stream when readmitted to the reaction zone. A suitable rate of gas flow can be readily determined by experimentation. Make-up of gaseous monomer to the circulating gas stream can be at a rate equal to the rate at which particulate polymer product and monomer associated therewith is withdrawn from the reactor and the composition of the gas passing through the reactor can be adjusted to maintain an essentially steady state gaseous composition within the reaction zone. The gas leaving the reaction zone 130 can be passed to the velocity reduction zone 132 where entrained particles are removed, for example, by slowing and falling back to the reaction zone 130. If desired, finer entrained particles and dust can be removed in a separation system 136, such as a cyclone and/or fines filter. The gas 124 can be passed through a heat exchanger 138 where at least a portion of the heat of polymerization can be removed. The gas can then be compressed in a compressor 140 and returned to the reaction zone 130.

The reactor temperature of the fluid bed process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Thus, the upper temperature limit in one embodiment is the melting temperature of the polyethylene copolymer produced in the reactor. However, higher temperatures may result in narrower MWDs, which can be improved by the addition of the MCN, or other, co-catalysts, as described herein.

Hydrogen gas can be used in olefin polymerization to control the final properties of the polyolefin, such as described in the "Polypropylene Handbook," at pages 76-78 (Hanser Publishers, 1996). Using certain catalyst systems, increasing concentrations (partial pressures) of hydrogen can increase the melt index (MI) or flow index (FI) of the polyethylene copolymer generated. The melt index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired melt index of the final polyolefin polymer. For example, the mole ratio of hydrogen to total monomer ($H_2$:monomer) can be greater than about 0.0001, greater than about 0.0005, or greater than about 0.001. Further, the mole ratio of hydrogen to total monomer ($H_2$:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm, based on weight. Further, the ratio of hydrogen to total monomer ($H_2$:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

As noted, a slurry polymerization process can also be used in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. In one embodiment, a hexane, isopentane, or isobutane medium can be employed. The slurry can be circulated in a continuous loop system.

The product polyethylene can have a melt index ratio (MIR or $I_{21}/I_2$) ranging from about 15 to about 300, or from about 15 to less than about 150, or, in many embodiments, from about 15 to about 50. Flow index (FI, HLMI, or $I_{21}$) can be measured in accordance with ASTM D1238 (190° C., 21.6 kg). The melt index (MI, $I_2$) can be measured in accordance with ASTM D1238 (at 190° C., 2.16 kg weight).

Density can be determined in accordance with ASTM D-792. Density is expressed as grams per cubic centimeter (g/cm$^3$) unless otherwise noted. The polyethylene can have a density ranging from a low of about 0.89 g/cm$^3$, about 0.90 g/cm$^3$, or about 0.91 g/cm$^3$ to a high of about 0.95 g/cm$^3$, about 0.96 g/cm$^3$, or about 0.97 g/cm$^3$. The polyethylene can have a bulk density, measured in accordance with ASTM D1895 method B, of from about 0.25 g/cm$^3$ to about 0.5 g/cm$^3$. For example, the bulk density of the polyethylene can range from a low of about 0.30 g/cm$^3$, about 0.32 g/cm$^3$, or about 0.33 g/cm$^3$ to a high of about 0.40 g/cm$^3$, about 0.44 g/cm$^3$, or about 0.48 g/cm$^3$.

The polyethylene can be suitable for such articles as films, fibers, nonwoven and/or woven fabrics, extruded articles, and/or molded articles. Examples of films include blown or cast films formed in single layer extrusion, coextrusion, or lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or non-woven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions by injection molding or rotation molding or blow molding processes in the form of bottles, tanks, large hollow articles, rigid food containers and toys, etc.

Examples

To provide a better understanding of the foregoing discussion, the following non-limiting examples are provided. All parts, proportions, and percentages are by weight unless otherwise indicated.

As described herein, comonomer, such as a $C_4$-$C_8$ alpha-olefin is added to a reaction, along with ethylene monomer, to create short chain branching (SCB) in polyethylene copolymers. The type, level, and distribution of SCB within a molecule and/or among different molecules in a polymer can have great effects on the polymer in crystalline morphology, tie chain probability, resin density, processability, stiffness, toughness, optical properties, melting distribution, and heat sealing properties.

In contrast, long chain branching (LCB) refers to branches whose lengths are comparable to the critical entanglement length of a linear polymer chain. Such branches have a strong effect on various aspects of the polymer rheology and, consequently, the polymer performance in a fabrication process. Due to its long relaxation nature, LCB can also have pronounced effects on the toughness of a fabricated article through orientation effect. Hydrogen may be added to the polymer reactions to control molecular weight. The hydrogen acts as chain termination agent, essentially replacing a monomer or comonomer molecule in the reaction. This stops the formation of a current polymer chain, and allows a new polymer chain to begin.

Polyethylene Polymers with Enhanced Stiffness, Toughness, and Processability

A number of polymer catalyst systems have been developed to provide for different stiffness, toughness, and processability (S/T/P) combinations through on-line compositional adjustments, for example, using the trim catalyst systems discussed with respect to FIG. 1. These catalyst systems take advantage of a set of catalyst compounds that show the potential to make broad orthogonal composition distribution (BOCD) products, or broad composition distribution (BCD) products in the absence of long chain branching (LCB), as defined herein. This combination allows for controlling parameters that provide S/T/P attributes beyond existing products.

The concepts were validated using polymerization runs performed in two pilot plant campaigns. Table 1 shows the polymers produced in the first pilot plant campaign. This campaign was performed using a catalyst pair including a catalyst matching formula (III) and a catalyst composition containing formulas (IV-A) and (IV-B), which were co-deposited on SMAO (silica-methylaluminoxane) at different ratios. All runs were performed at a temperature of about 78° C., e.g., from about 77.3° C. to about 78.9° C.

The first campaign validated the concept of making a wide range of products with a fixed pair of mixed catalysts, wherein different products could be obtained by changing the ratios of the two catalysts. The products were made with an MI and a density similar to those of existing products so that blown film evaluations could be carried out.

In Table 1, polymers 1-1, 1-8, 1-9, and 1-10 are control samples made for comparison with the experimental polymers 1-2 through 1-7 described in embodiments. The control polymers 1-8 and 1-9 were made using the catalyst dimethylsilyl-bis-(tetrahydroindenyl) zirconium dichloride, $Me_2Si(H_4Ind)_2ZrCl_2$. This catalyst system, and the corresponding polymers it can make, is discussed in U.S. Pat. No. 6,255, 426 to Lue, et al., hereinafter "the '426 patent." Polymers 1-1 and 1-10 were made using a neat catalyst matching structure (III) supported on SMAO.

Blown film evaluation on the polymers from the first campaign using an exemplary mixed catalyst system (polymers 1-2 through 1-4) showed substantial improvements in S/T/P properties for the combination, in comparison to polymers produced using other catalysts. The processability of the polymers is represented by the MIR, shown in Table 1, which is the ratio of the I-21/I-2. A higher MIR represents a more easily processed polymer.

Figure 2:
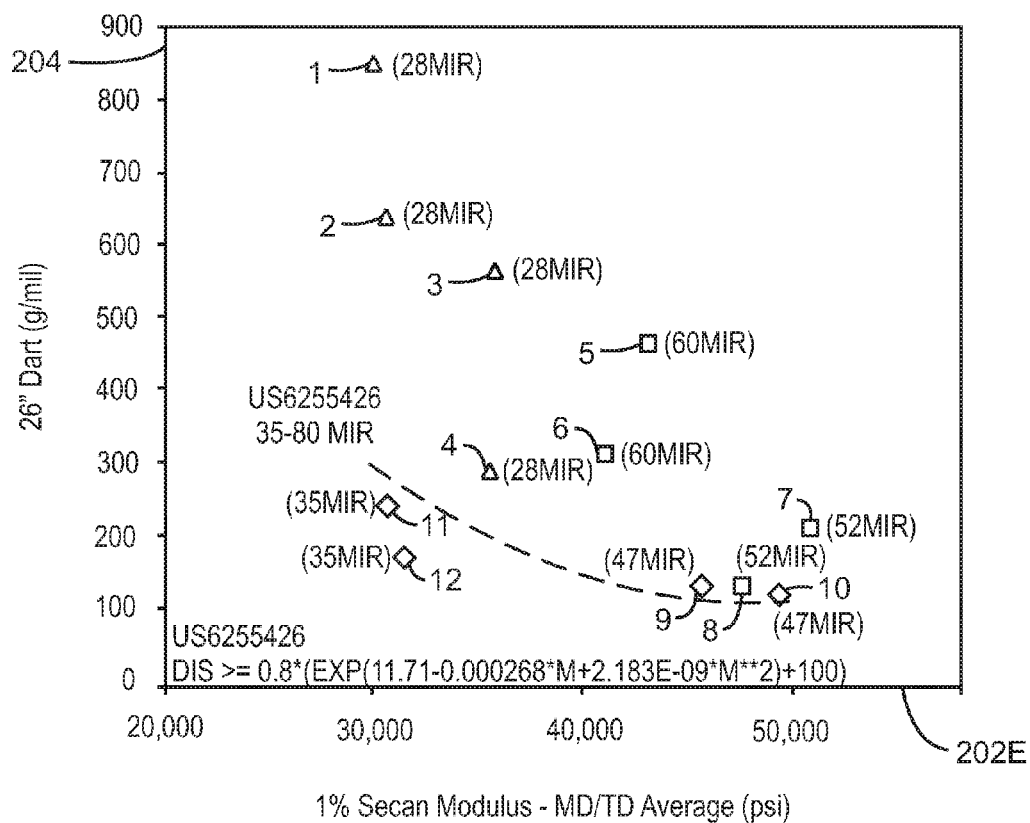
FIG. 2 is a plot comparing stiffness, toughness, and processability for a number of different polymers.

FIG. 2 is a plot 200 comparing stiffness, toughness, and processability for a number of different polymers. The x-axis 202 represents stiffness, as measured by average machine direction and transverse direction results for 1% secant modulus. The y-axis 204 represents dart drop in g/mil. The numerical values shown on the plot 200 correspond to the result numbers listed in Table 2. The dashed line 206 corresponds to a relationship between modulus and dart impact that was developed for the polymers described in the '426 patent, i.e., control polymers 1-8 and 1-9 (results 9-12 in Table 2 and FIG. 2). For testing, two different film gauges (FG) were generated for each polymer, 1 mil (25.4 µm) and 2 mil (50.8 µm), both extruded from a single die gap of 60 mil (1.52 mm) at a 2.5 blow-up ratio (BUR). For the exemplary polymers, results 5-8, thicker films show an increase in both dart drop and stiffness.

As shown in FIG. 2, exemplary polymers 1-2 and 1-4 (results 5-8 in Table 2 and FIG. 2) have a similar dart drop to modulus relationship as the control polymer 1-1 and 1-10 (results 1-4 in Table 2 and FIG. 2), e.g., exponentially decreasing in dart drop as the modulus increases. However, compared to the relationship 206 for the control polymers 1-8 and 1-9, the experimental polymers 1-2 and 1-4 exhibit a substantially improved dart drop to modulus relationship. Further, the MIR for experimental polymers 1-2 and 1-4 is higher (50-60 s vs. 20-30 s) than the controls 1-1 & 1-10, indicating that the exemplary polymers are more easily processed at equivalent or similar MI.

The differences achieved are further illustrated in Table 3. Table 3 is a table of results obtained from polymers made in a first pilot plant run. The experimental polymers are shown as columns 1-2 and 1-4, where the identities correspond to the polymers in Table 1. As discussed with respect to FIG. 2, the values for MIR for the two experimental polymers is higher than the values for control polymers 1-10, 1-1, 1-9, and 1-8, indicating the nature of easier processability. This is further confirmed by the values obtained for motor loading, which indicates the power required to blow the film samples at a given output rate as a proportion of the total power available. The values for motor loading for the two experimental polymers are generally lower than the values for control polymers and become most evident when the comparisons were made on the basis of similar MI, e.g., experimental polymer 1-2 vs. control polymers 1-10, 1-11 and 1-9. Similarly, comparison of values for Energy Specific Output (E.S.O) in Table 3 clearly demonstrated that experimental polymer 1-2 had a higher output rate for a given power input to the extruder than the control polymers 1-10, 1-11 and 1-9. In addition to the improvements in processability, the increases in the values for stiffness and dart drop are shown in Table 3, although these are more clearly illustrated in the plot of FIG. 2

Alternate Embodiments Tested

The second pilot plant campaign used a spray-dried version of the catalyst of formula (III) as a base catalyst, and mixed it with four different "trim-catalysts" on line, e.g., formulas (IV-A and B), (IV-C), (IV-D), and (V-A). Table 4 shows polymers generated in the second pilot plant run. It should be noted that the data provides a single picture of the production for a particular grade with small scale sampling and homogenization. Thus, the values are merely examples of values that can be produced with the present polymer systems. The key objective for the second campaign was to validate the tuning concept and investigate how product composition was changed. No attempt was made to achieve particular MI/Density targets. A number of different polymer types were made following the procedures described herein.

These polymer types illustrate the flexibility of the current procedures for creating tunable products using a trimmed catalyst approach and are discussed with respect to Tables 5-8 below.

Film tests were performed on selected resins generated in this pilot plant run and one of the resins generated in the first pilot plant run, with the results shown in Tables 5 and 6. In Table 5, the control was a different lot of the same commercial grade as polymer 1-8 (Table 1), labeled 1-8B. The results in Table 5 show that films made from all experimental polymers 1-3 (Table 1), 2-3b and 2-4b are similar in stiffness to the control, but have a higher value for MD tear and a substantially higher value for dart drop, indicating improved toughness. Further, all experimental polymer 1-3, 2-3b, and 2-4B also had lower values for motor loading and higher values for energy specific output (E.S.O), indicating improved processability, although this may also be partly due to a higher melt index (I-2).

Table 6 compares results obtained for experimental polymer 2-6A, using another trim system (shown in Table 4), to control the polymer properties. Four polyethylene resins are used as the control polymers: Exceed 1327CA, available from ExxonMobil Chemical; ML2610PNX, made using an HfP catalyst system; LL3201.69, which is a Ziegler-Natta catalyst with a 1-hexene comonomer; and Enable 2705CH, which is a commercial LLDPE. The experimental polymer 2-6A is similar in stiffness to the controls. However, the experimental polymer 2-6A is substantially higher in dart drop than either of the comparison polymers, indicating that it is much tougher than the controls. Further, the tear values are substantially higher than the control values, confirming the increase in the toughness. Polymers of this type may make resins that are effective replacements for polymers made using Ziegler-Natta (ZN) type catalysts.

A comparison of the film properties of catalysts made with the trim systems described herein was made in comparison to blends of polymers made with Ziegler catalysts. During the third pilot plant campaign, two trim copolymer products with butene (C4) as comonomer were made as catalyst system A and catalyst system B, both using catalysts having formula (III) and trimmed with a mixture of catalysts of formulas (IV-A) and (IV-B). With a conventional catalyst system like Ziegler-Natta, the comonomer 1-butene (C4) is known to produce a lower quality product than a product made with a 1-hexene comonomer, however, the economics are more favorable. Based on the developments discussed herein, it was believed that the products described herein would have some degree of BOCD characteristics and therefore certain form of improvements in stiffness, toughness, and processability (S/T/P) over the conventional ZN-LLC4 products. More specifically, it was hoped that the experimental polymers would offer S/T/P advantages over a LL-rich blend of (ZNLLC4+HP-LDPE) and/or ZN-LLC6 like toughness (e.g., Dart).

The data in Table 7 shows the data for the comparison between the experimental C4 polymers versus a control blend of polymers, LLC4/HPLD, formed from Ziegler-Natta catalyzed LLC4 product and LDPE by High Pressure polymerization process (HPLD). Although the experimental C4 polymers did not show substantial improvements across all of the various S/T/P measurements, dart impact and machine direction (MD) tear of the experimental polymers showed results that were approaching those of a conventional ZN-LLC6 product.

It can be seen from the data in Tables 4-7, that the trim process can be successfully used to create polymers having the characteristics described herein. Accordingly, various embodiments use the trim process in a gas-phase polymerization process to produce the target polymers.

During another pilot plant campaign, two additional trim copolymer products with butene (C4) as comonomer were made using catalyst formula comprising a mixture of III and IV-A,B (85% III and 15% IV-A,B on a molar basis) and trimmed with a solution of IV-A,B. The film and resin properties of the butene copolymers are compared with control samples LL1001x26 and LL3001.63 (commercial C4 and C6 LLDPE, respectively, made with conventional Ziegler-Natta catalyst system and available from ExxonMobil Chemical Company) in Table 8. This campaign used a spray-dried version that includes around 85% of the catalyst of formula (III) as a base catalyst and 15% of formula (IV-A and B) on the support. The co-supported catalyst is mixed it with further amount of trim-catalyst of formulas (IV-A and B). As shown in Table 8, this resulted in polymers that showed good properties in comparison to LLDPE polymers made using a Ziegler-Natta catalyst and a butene copolymer.

Differentiation on Long Chain Branching (LCB)

The advantages provided by resins generated using the techniques described herein may be described by comparing the absence of LCB in the present resins to the presence of LCB in control resins (Polymer 1-8 & 1-9). This may be performed using a van Gurp-Palmen (vGP) plot, which has been described in the literature as a mean of detecting the presence of LCB. See César A. Garcia-Franco, et al., "Similarities between Gelation and Long Chain Branching Viscoelastic Behavior," Macromolecules, Vol. 34, No. 10, pp. 3115-3117.

Figure 3:
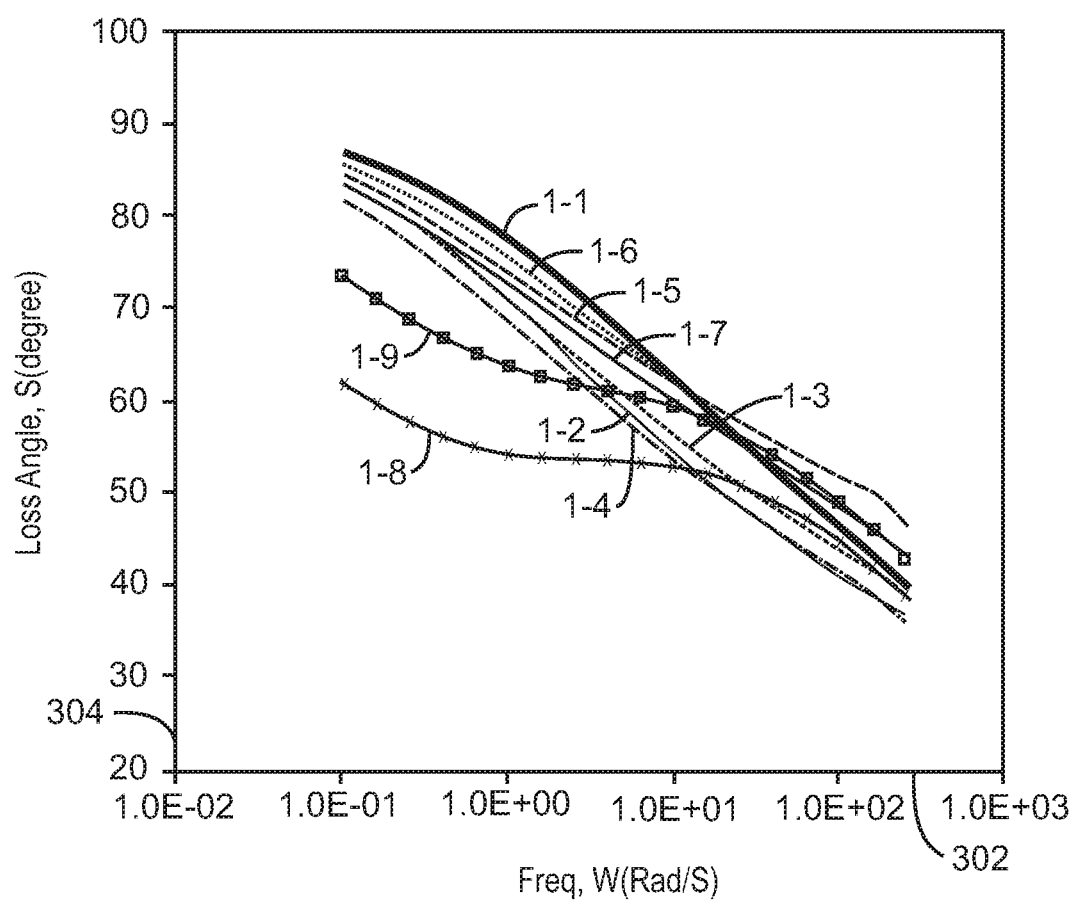
FIG. 3 is a van Gurp-Palmen (vGP) plot showing a comparison of products generated in the first pilot plant run.

FIG. 3 is a van Gurp-Palmen (vGP) plot 300 showing a comparison of products generated in the first pilot plant run. The x-axis 302 represents the frequency in radians/second while the y-axis 304 represents the loss angle in degrees. Each of the plots is labeled with the corresponding identification from Table 1. In the range of interest for ω, i.e., from 0.1 to 251 Rad/s, the control polymers 1-8 and 1-9 showed an inflection point (including a concave section). Further, both the control polymers 1-8 and 1-9 are known for the presence of LCB. In contrast, all of the experimental polymers 1-1 through 1-7 showed no inflection point. The inflection point may be further distinguished by a first derivative plot of the vGP plot, as shown in FIG. 4.

Dynamic Shear Viscosity and the Van Gurp-Palmen Plot

Small amplitude oscillatory shear test was performed using a Dynamic Stress Rheometer by Rheometric Scientific at 190° C., using parallel plate geometry of 25 mm plate diameter and 1.5 mm gap. The test was done under a controlled stress of 2000 dynes/cm$^2$ at frequencies from 0.1 to 251 rad/sec with log sweep mode at 5 points per decade. Data for generating the van Gurp-Palmen plots, as shown in FIG. 3, was available directly from the test results, e.g., by plotting phase angle against the frequency.

Figure 4:
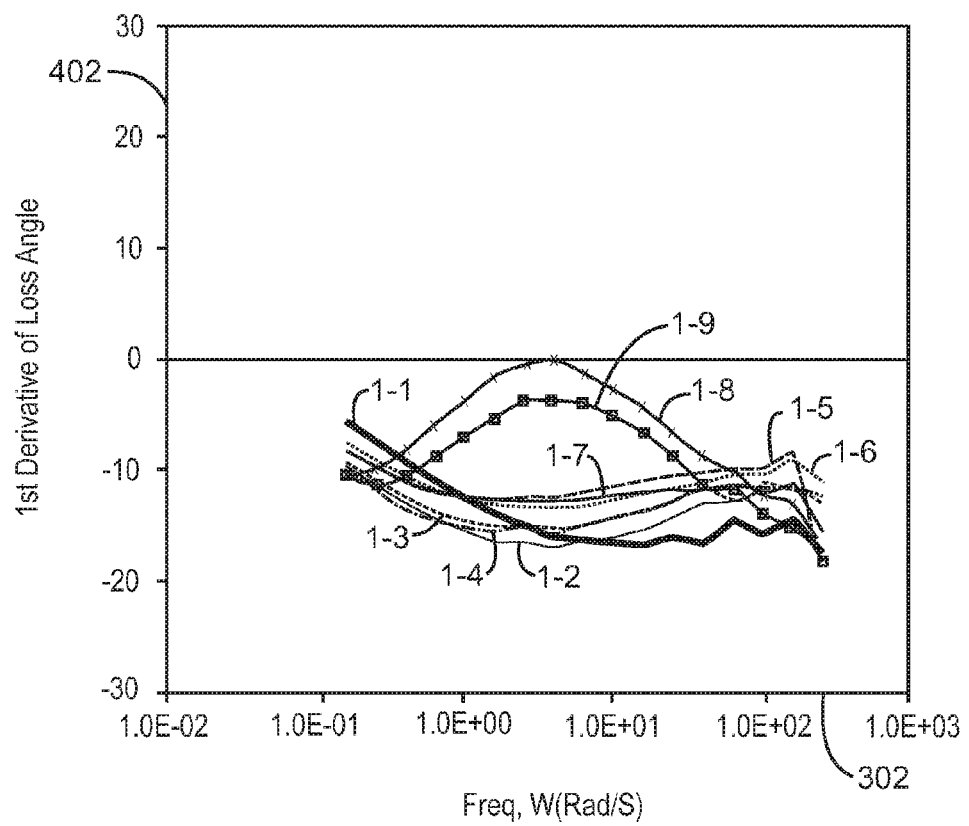
FIG. 4 is a plot of the first derivative of the results shown in the vGP plot of FIG. 3.

FIG. 4 is a plot 400 of the first derivative of the results shown in the vGP plot 300 of FIG. 3. The like numbered item is as described with respect to FIG. 3. The value of the first derivative for FIG. 4 was calculated for each pair of consecutive data points as $1^{st}$ Derivative=[(Phase Angle)$_{i+1}$−(Phase Angle)$_i$]/[log(Frequency)$_{i+1}$−log(Frequency)$_i$]. In the plot 400, the y-axis 402 represents the first derivative of the loss angle from the vGP plot 300. As shown in the plot 400, the control polymers 1-8 and 1-9 (Table 1) show a very distinctive peak in the first derivative, confirming the inflection point. In contrast, the first derivatives for the experimental polymers 1-2 through 1-7 show a negative deflection in the same location as the peak for the control polymers 1-8 and 1-9. Although some of the experimental polymers show a sharp peak in the final values, at a frequency of between about 100-200 Rad/S, this is due to noise in the measurements. Similar results were obtained for the experimental polymers generated in the second pilot plant runs.

Figure 5:
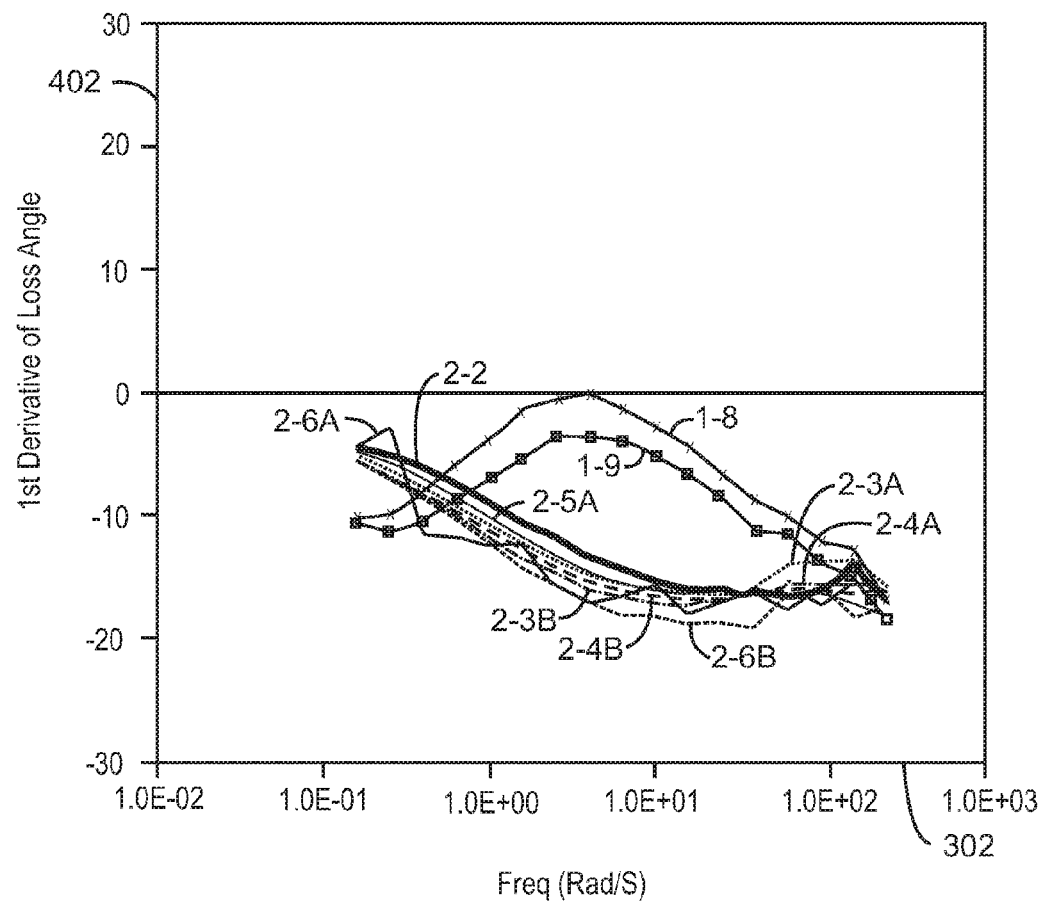
FIG. 5 is a plot of the first derivative of the vGP plot for resins made in the second pilot plant run.

FIG. 5 is a plot 500 of the first derivative of the vGP plot for resins made in the second pilot plant run. Like numbered items are as discussed with respect to FIGS. 3 and 4. As for the results shown in FIG. 4, the experimental polymers 2-3A through 2-6B (Table 4) show a negative deflection in the same location as the peak for the control polymers 1-8 and 1-9.

In addition to the lack of long chain branching, for example, as indicated in the vGP plot, the experimental polymers for both the first and second pilot plant runs were found to have a unique molecular weight distribution (MWD) and short chain branching distribution (SCBD). This was determined by a number of techniques, including nuclear magnetic resonance (NMR) to determine SCB content, gel permeation chromatography (GPC) to determine MWD, and temperature rising composition distribution (TREF) to fractionate the polymers to determine SCBD.

Measuring Tw1, Tw2, Mw1 & Mw2 from CFC

A new technique has been developed for determining both MWD and SCBD compositional information, using cryogenic cross fractionation (cryo CFC), to compare the experimental polymers to competitive products on the market. The procedures for the determination of CFC data are discussed in more detail in the examples presented below.

Figure 6A:
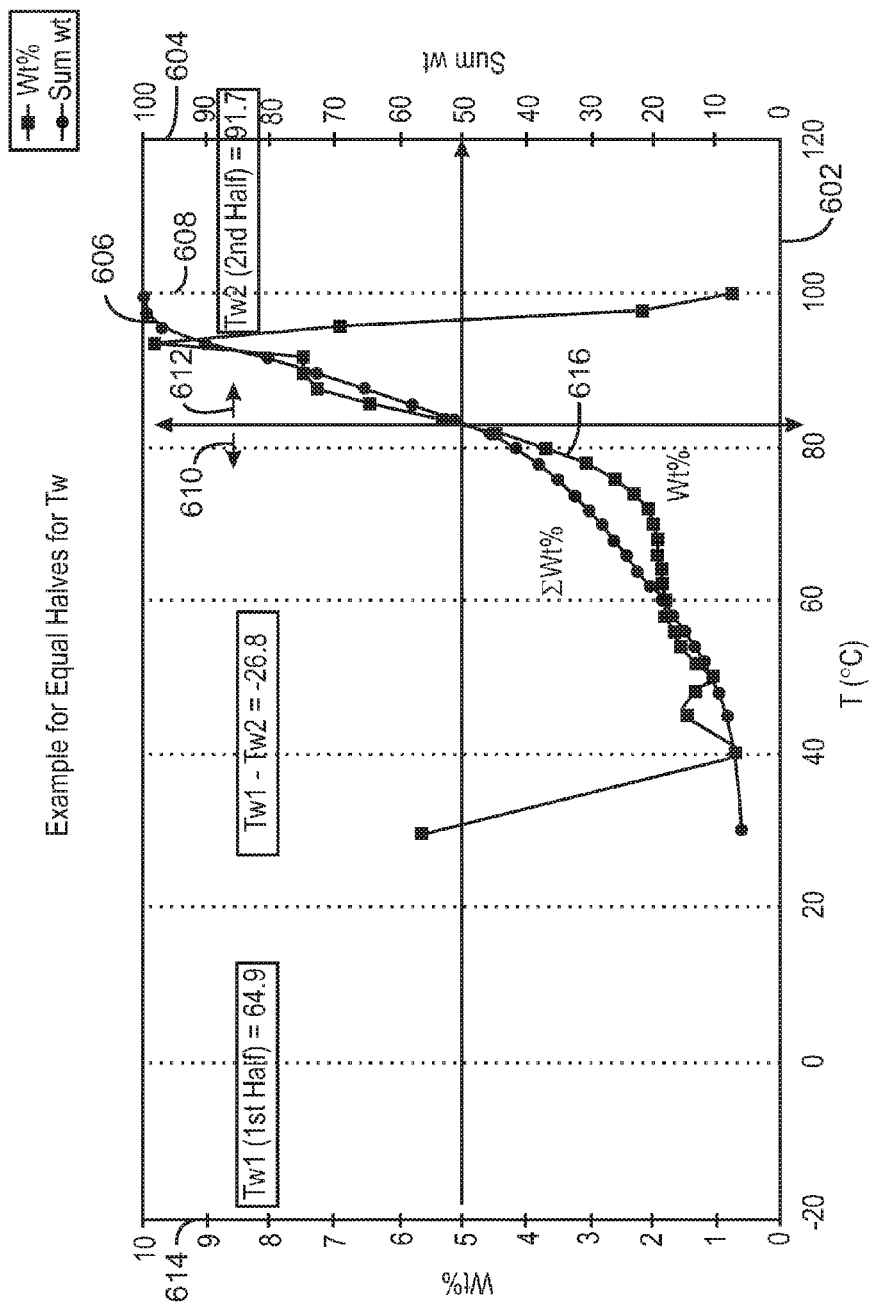
FIGS. 6A and 6B are plots that illustrate the calculations used to determine the CFC result.
Figure 6B:
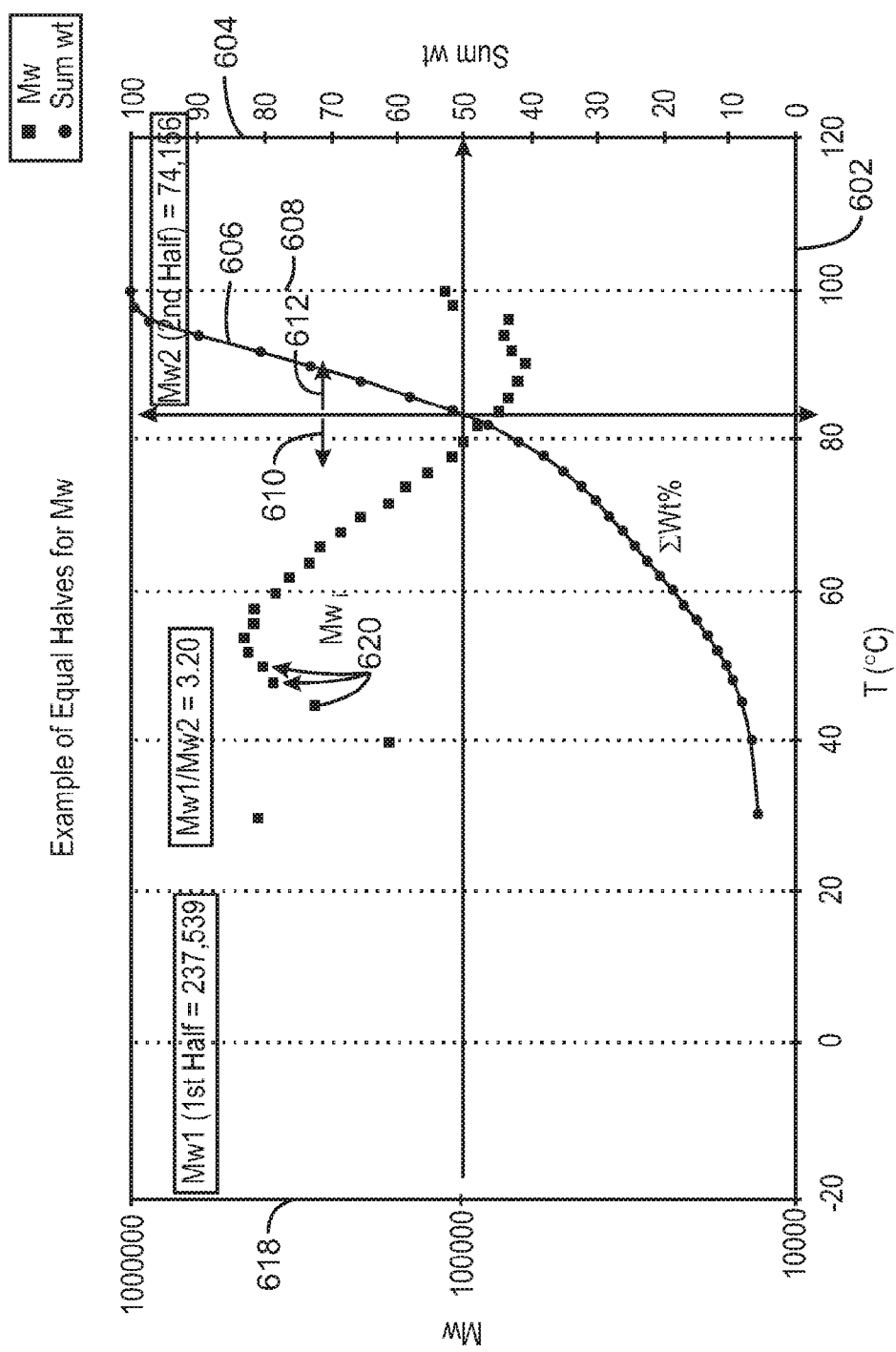

FIGS. 6A and 6B are plots that graphically illustrate the calculations used to determine the CFC result. Only fractions having MWD data are considered. In both FIGS. 6A and 6B, the x-axis 602 represents the elution temperature in centigrade, while the right hand y-axis 604 represents the value of the integral 606 of the molecular weights that have been eluted. The temperature 608 at which 100% of the material has eluted in this example is about 100° C. The point at which 50% of the polymer has eluted is determined by the integral 606, which is used to divide each of the plots into a lower half 610 and an upper half 612.

The values Tw1, Tw2, Mw1 & Mw2 which are shown in FIGS. 6A and B and specified in various claims of this invention are derived from the CFC data file as reported from the instrument software. In the section of "Fraction summary" in the CFC data file, each fraction is listed by its fractionation temperature ($T_i$) along with its normalized wt. % value ($W_i$), cumulative wt. %, i.e., Sum wt. on FIGS. 6A and B, and various moments of molecular weight averages (including $Mw_i$).

To calculate values of Tw1, Tw2, Mw1 & Mw2, the data in "Fraction summary" was divided into two roughly equal halves. Weight averages of $T_i$ and $Mw_i$ for each half were calculated according to the conventional definition of weight average. Fractions which did not have sufficient quantity (i.e., <0.5 wt. %) to be processed for molecular weight averages in the original data file were excluded from the calculation of Tw1, Tw2, Mw1 & Mw2.

The first part of the process is illustrated by FIG. 6A. From the section of fraction summary in the CFC data file, the fraction whose cumulative wt. % (i.e., Sum wt) is closest to 50 is identifies identify (e.g., the fraction at 84° C. on FIG. 6A). The Fraction summary data is divided into two halves, e.g., Ti<=84° C. as the $1^{st}$ half and Ti>84° C. as the $2^{nd}$ half on FIG. 6A. Fractions which do not have molecular weight averages reported in the original data file are excluded, e.g., excluding the fractions with Ti between 25° C. and 40° C. on FIG. 6A.

In FIG. 6A, the left hand y-axis 610 represents the wt % 612 of the eluted fraction. Using the procedure above to divide the curves into two halves, these values are used to calculate the weight average elution temperature for each half using the formula shown in Eqn. 1.

$$Tw = \frac{\sum T_i W_i}{\sum W_i} \qquad \text{Eqn. 1}$$

In Eqn. 1, Ti represents the elution temperature for each eluted fraction, and Wi represents the normalized weight % (polymer amount) of each eluted fraction. For the example shown in FIG. 6A, this provides a weight average elution temperature of 64.0° C. for the first half, and 91.7° C. for the second half.

In FIG. 6B, the left hand axis 618 represents the weight average molecular weight ($Mw_i$) 620 of each eluted fraction. These values are used to calculate the weight average molecular weight for each half using the formula shown in Eqn. 2.

$$Mw = \frac{\sum Mw_i W_i}{\sum W_i} \qquad \text{Eqn. 2}$$

In Eqn. 2, $Mw_i$ represents the weight average molecular weight of each eluted fraction, and $W_i$ represents the normalized weight % (polymer amount) of each eluted fraction. For the example shown in FIG. 6B, this provides a weight average molecular weight of 237,539 for the first half, and 74,156 for the second half. The values calculated using the techniques described above may be used to classify the MWD×SCBD for experimental polymers and control polymers as shown in Table 8 and FIG. 7.

Figure 7:
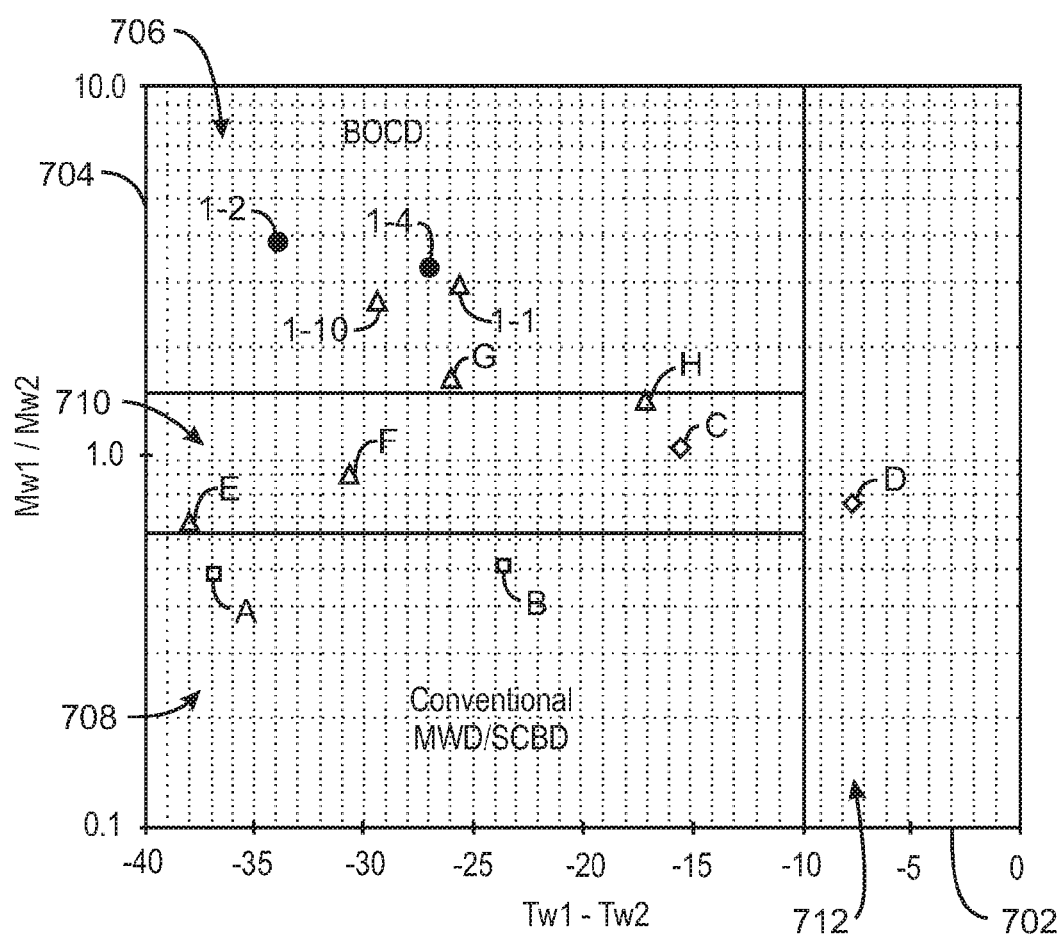
FIG. 7 is a plot of (Mw-1/Mw-2) vs. (Tw-1–Tw-2) for the experimental polymers versus a variety of competitive polymers on the market.

FIG. 7 is a semi-log plot 700 of (Mw-1/Mw-2) vs. (Tw-1−Tw-2) for the experimental polymers versus a variety of competitive polymers on the market. In the plot 700, the x-axis 702 represents the value of the difference between the first and second weight average elution temperatures. The y-axis 704 in a log scale represents the ratio of the first weight average molecular weight to the second weight average molecular weight. Each of the polymers is identified in Table 9, which also lists the calculated values for the weight average molecular weights and the weight average elution temperatures. The experimental polymers came from the first pilot plant run, and are defined in Table 1.

Four regions can be generally defined by the plot 700. Polymers that fall in a BOCD region 706 have a broad, orthogonal composition distribution. A BOCD indicates that lower molecular weight polymer chains in the polymer have a high density, e.g., due to a lack of short chain branching (SCB), while higher molecular weight segments have a low density, e.g. due to higher amounts of SCB. In a conventional region 708, polymers have longer polymer chains that have a higher density than shorter polymer chains, which is a mirror image of the BOCD region. In a center region 710, polymers have a uniform, but not necessarily narrow MWD, e.g., Mw1 and Mw2 for the two halves are similar to each other but the MWDs within each half could be narrow or broad. In a side region 712, polymers have a uniform, but not necessarily narrow composition distribution, e.g., the values of Tw1 and Tw2 for the two halves are close to each other but the shape of the TREF curve within each half does not have to be narrow. As a hypothetical example, a polymer that exhibits one single major peak with a tail or tails at one or both ends of its TREF curve could fall into this category after being divided into two equal halves. The Tw1 and Tw2 values for this hypothetical polymer could be close to each other but its tails on TREF curve could disqualify the polymer from having a narrow SCBD.

As can be seen, experimental polymers 1-2 and 1-4, and control polymers 1-1 and 1-10 are in the BOCD region 706, indicating a different MWD and SCBD from most of the commercial polymers. Control polymers 1-1 and 1-10 differ from the experimental polymers in MIR, which is substantially lower for the control polymers 1-1 and 1-10 than for the experimental polymers 1-2 and 1-4. One commercial polymer G is slightly in the BOCD region 706, but also has a low MIR (about 30).

Thus, the use of the technique described above can identify polymers that have BOCDs. Accordingly, the technique can be use both to screen new polymers for the distribution and to control polymer production to target particular locations in the BOCD region 706.

Physical Testing Procedures

Haze

Film total haze is measured according to ASTM D1003-13, "Alternative Haze (Shortcut) Procedure." The measurements were made on a HazeGard PLUS haze meter from BYK-Gardner, Inc.

Internal haze was measured using techniques to minimize interference from surface effects. The procedure followed was cutting at least 3 samples, at least 1" wide specimens transversely across the film sample. Immersion oil was placed on two microscope slides, and each specimen was sandwiched between the slides. The microscope slides were standard 75 mm×50 mm slides. The immersion oil used was Cat. No. 16484 from Cargille Laboratories in NJ, USA. The ends of the slide were taped to trap and possibly straighten the specimen before following the procedure for total haze on the taped slide specimen. The measurements were performed on the part of the specimen that did not have air bubbles. Areas where the immersion oil had come outside and around the glass slide were also avoided.

Cross-Fractionation Chromatography (CFC)

Cross-fractionation chromatography (CFC) was performed on a CFC-2 instrument from Polymer Char, Valencia, Spain. The instrument was operated and subsequent data processing, e.g., smoothing parameters, setting baselines, and defining integration limits, was performed according to the manner described in the CFC User Manual provided with the instrument or in a manner commonly used in the art. The instrument was equipped with a TREF column (stainless steel; o.d., ⅜"; length, 15 cm; packing, non-porous stainless steel micro-balls) in the first dimension and a GPC column set (3×PLgel 10 μm Mixed B column from Polymer Labs, UK) in the second dimension. Downstream from the GPC column was an infrared detector (IR4 from Polymer Char) capable of generating an absorbance signal that is proportional to the concentration of polymer in solution.

The sample to be analyzed was dissolved in ortho-dichlorobenzene, at a concentration of about 5 mg/ml, by stirring at 150° C. for 75 min. Then a 0.5-ml volume of the solution containing 2.5 mg of polymer was loaded in the center of the TREF column and the column temperature was reduced and stabilized at ≈120° C. for 30 min. The column was then cooled slowly (0.2° C./min) to 30° C. (for ambient runs) or −15° C. (for cryogenic runs) to crystallize the polymer on the inert support. The low temperature was held for 10 min before injecting the soluble fraction into the GPC column. All GPC analyses were done using solvent ortho-dichlorobenzene at 1 ml/min, a column temperature of 140° C., and in the "Overlap GPC Injections" mode. Then the subsequent higher-temperature fractions were analyzed by increasing the TREF column temperature to the fraction set-points in a stepwise manner, letting the polymer dissolve for 16 min ("Analysis Time"), and injecting the dissolved polymer into the GPC column for 3 min ("Elution Time").

The universal calibration method was used for determining the molecular mass of eluting polymers. Thirteen narrow molecular-weight distribution polystyrene standards (obtained from Polymer Labs, UK) within the range of 1.5-8200 Kg/mol were used to generate a universal calibration curve. Mark-Houwink parameters were obtained from Appendix I of "Size Exclusion Chromatography" by S. Mori and H. G. Barth (Springer). For polystyrene K=1.38×10$^{-4}$ dl/g and α=0.7; and for polyethylene K=5.05×10−4 dl/g and α=0.693 were used. Fractions having a weight % recovery (as reported by the instrument software) of less than 0.5% were not processed for calculations of molecular-weight averages (Mn, Mw, etc.) of the individual fractions or of aggregates of fractions.

Data Tables for Polymers:

TABLE 1

Polymers produced in first pilot plant campaign

| Polymer ID | Catalyst System | Cat. Form | Hexene | H$_2$ | MI | Density | MIR |
|---|---|---|---|---|---|---|---|
| 1-1 | III | Dry | 0.099 | 4.2 | 0.96 | 0.921 | 28 |
| 1-2 | 75 III/ 25 IV-A and IV-B | CD | 0.132 | 4.5 | 0.99 | 0.922 | 60 |
| 1-3 | 75 III/ 25 IV-A and IV-B | CD | 0.099 | 4.2 | 1.2 | 0.927 | 54 |
| 1-4 | 75 III/ 25 IV-A and IV-B | CD | 0.104 | 3.3 | 0.74 | 0.926 | 52 |
| 1-5 | 50 III/ 50 IV-A and IV-B | CD | 0.099 | 4.2 | 4.8 | 0.932 | 50 |
| 1-6 | 50 III/ 50 IV-A and IV-B | CD | 0.133 | 4.6 | 5.9 | 0.926 | 51 |
| 1-7 | 50 III/ 50 IV-A and IV-B | CD | 0.134 | 2.7 | 2.2 | 0.924 | 46 |
| 1-8 (commercial; different lots shown as 1-8B and 1-8C) | Enable 2705CH | | | | 0.46 | 0.927 | 47 |
| 1-9 | Enable 2010CH | | | | 0.96 | 0.920 | 35 |
| 1-10 | VPR/G1750 | | | | 0.9 | 0.919 | 28 |

TABLE 2

Catalyst identities and polymer parameters for FIG. 2

| Result Number | Polymer Identification (from Table 1) | Film Thickness (mil) |
|---|---|---|
| 1 | 1-10 | 2 |
| 2 | 1-10 | 1 |
| 3 | 1-1 | 2 |
| 4 | 1-1 | 1 |
| 5 | 1-2 | 2 |
| 6 | 1-2 | 1 |
| 7 | 1-4 | 2 |
| 8 | 1-4 | 1 |
| 9 | 1-8 | 2 |
| 10 | 1-8 | 1 |
| 11 | 1-9 | 2 |
| 12 | 1-9 | 1 |

TABLE 3

Data from Polymers in First Pilot Plant Run

| | Polymer ID (from Table 1): | | | | | |
|---|---|---|---|---|---|---|
| | 1-10 | 1-1 | 1-2 | 1-4 | 1-9 | 1-8 |
| Density (g/cm3) | 0.919 | 0.921 | 0.922 | 0.926 | 0.920 | 0.927 |
| I-2 (dg/min) | 0.9 | 1.0 | 1.0 | 0.7 | 1.0 | 0.5 |
| MIR (I-21/I-2) | 28 | 28 | 60 | 52 | 35 | 47 |
| *1.0 mil FG @ 2.5 BUR/60 mil DG* | | | | | | |
| Motor Load (%) | 44.1 | 48.0 | 32.8 | 41.9 | 40.6 | 48.7 |
| E.S.O. (lb/HP-hr) | 13.13 | 12.14 | 15.63 | 13.17 | 14.26 | 11.65 |
| MD Modulus (psi) | 26,996 | 32,040 | 32,858 | 41,030 | 28,593 | 44,954 |
| TD Modulus (psi) | 32,673 | 39,069 | 49,118 | 54,096 | 34,506 | 53,592 |
| 26" Dart (g/mil) | 851 | 291 | 317 | 136 | 173 | 124 |
| Average Mod (psi) | 29,835 | 35,555 | 40,988 | 47,563 | 31,550 | 49,273 |
| Cal. Dart per. '426 patent (g/mil) | 309 | 192 | 145 | 120 | 262 | 116 |
| Msrd. Dart vs. '426 (% diff.) | 275% | 152% | 219% | 114% | 66% | 107% |

| | Polymer ID (from Table 1): | | | | | |
|---|---|---|---|---|---|---|
| | 1-10 | 1-1 | 1-2 | 1-4 | 1-9 | 1-8 |
| Density (g/cm3) | 0.919 | 0.921 | 0.922 | 0.926 | 0.920 | 0.927 |
| I-2 (dg/min) | 0.9 | 1.0 | 1.0 | 0.7 | 1.0 | 0.5 |
| MIR (I-21/I-2) | 28 | 28 | 60 | 52 | 35 | 47 |
| *2.0 mil FG @ 2.5 BUR/60 mil DG* | | | | | | |
| Motor Load (%) | 47.0 | 48.3 | 33.5 | 42.2 | 42.1 | 48.5 |
| E.S.O. (lb/HP-hr) | 12.48 | 11.98 | 16.15 | 13.17 | 13.94 | 11.62 |
| MD Modulus (psi) | 27,921 | 32,000 | 32,675 | 41,145 | 28,911 | 43,437 |
| TD Modulus (psi) | 33,075 | 39,499 | 53,259 | 60,506 | 32,468 | 47,844 |
| 26" Dart (g/mil) | >641 (No Break) | 567 | 469 | 217 | 242 | 137 |
| Average Mod (psi) | 30,498 | 35,750 | 42,967 | 50,826 | 30,690 | 45,641 |
| Cal. Dart per. '426 patent (g/mil) | 289 | 189 | 135 | 113 | 284 | 125 |
| Msrd. Dart vs. '426 (% diff.) | >222% | 299% | 348% | 192% | 85% | 110% |

TABLE 4

Polymers produced in second pilot plant campaign using trim addition

| PDD col/Ident | Polymer No | Catalyst Type | Catalyst Form-Dry/Slurry | Catalyst Support | Al/Hf Catalyst Mole Ratio | Trim Catalyst Type | H2/C2 Conc Ratio (ppm/m %) | C6/C2 Conc Ratio (m/m) | Melt Index (dg/min) | High Load Melt Index (dg/min) | MIR (HLMI/MI) | Density (g/cc) | Cat Prod. |
|---|---|---|---|---|---|---|---|---|---|---|---|---|---|
| G/0.1 | 2-0.1 | III | Dry | | 98.6 | None | 6.03 | 0.016352 | 1.21 | 41.8 | 34 | 0.9180 | 13,239 |
| H/0.2 | 2-0.2 | III | Dry | | 98.6 | None | 5.81 | 0.014848 | 1.45 | 32.8 | 23 | 0.9168 | 13,071 |
| I/1 | 2-1 | III | Slurry | Spray Dried | 234 | None | 4.65 | 0.01527 | 0.73 | 18.2 | 25.0 | 0.9201 | 7,801 |

TABLE 4-continued

Polymers produced in second pilot plant campaign using trim addition

| PDD col/ Ident | Polymer No | Catalyst Type | Catalyst Form- Dry/Slurry | Catalyst Support | Al/Hf Catalyst Mole Ratio | Trim Catalyst Type | H2/C2 Conc Ratio (ppm/m %) | C6/C2 Conc Ratio (m/m) | Melt Index (dg/min) | High Load Melt Index (dg/min) | MIR (HLMI/MI) | Density (g/cc) | Cat Prod. |
|---|---|---|---|---|---|---|---|---|---|---|---|---|---|
| J/2 | 2-2 | III | Slurry | Spray Dried | 234 | None | 3.87 | 0.01539 | 0.49 | 11.7 | 23.9 | 0.9194 | 7,373 |
| K/3A | 2-3A | III | Slurry | Spray Dried | 234 | IV-A, IV-B | 3.79 | 0.01835 | 1.68 | 83.2 | 49.4 | 0.9340 | 9,956 |
| L/3B | 2-3B | III | Slurry | Spray Dried | 234 | IV-A, IV-B | 3.78 | 0.01729 | 1.01 | 37.0 | 36.6 | 0.9281 | 8,300 |
| N/4A | 2-4A | III | Slurry | Spray Dried | 234 | IV-C | 3.80 | 0.01823 | 1.72 | 57.0 | 33.1 | 0.9315 | 8,767 |
| M/4B | 2-4B | III | Slurry | Spray Dried | 234 | IV-C | 3.81 | 0.01742 | 1.23 | 35.9 | 29.1 | 0.9274 | 8,233 |
| P/5A | 2-5A | III | Slurry | Spray Dried | 234 | IV-D | 3.79 | 0.01709 | 1.090 | 27.8 | 25.5 | 0.9238 | 7,680 |
| O/5B | 2-5B | III | Slurry | Spray Dried | 234 | IV-D | 3.83 | 0.01614 | 0.914 | 21.3 | 23.3 | 0.9221 | 8,267 |
| R/6A | 2-6A | III | Slurry | Spray Dried | 234 | V-A | 3.79 | 0.01724 | 0.702 | 19.0 | 27.1 | 0.9234 | 7,233 |
| Q/6B | 2-6B | III | Slurry | Spray Dried | 234 | V-A | 3.80 | 0.01595 | 0.602 | 14.6 | 24.3 | 0.9201 | 8,178 |

TABLE 5

Comparative film results from second pilot plant run

| | Polymer identification: (From Tables 1 and 3) | | | | | | | |
|---|---|---|---|---|---|---|---|---|
| | 1-8B | 1-3 | 2-3B | 2-4B | 1-8C | 1-3 | 2-3B | 2-4B |
| Density (g/cm3) | 0.928 | 0.927 | 0.930 | 0.929 | 0.928 | 0.927 | 0.930 | 0.929 |
| I-2 (dg/min) | 0.5 | 1.2 | 1.0 | 1.2 | 0.5 | 1.2 | 1.0 | 1.2 |
| MIR (I-21/I-2) | 45 | 54 | 37 | 33 | 45 | 54 | 37 | 33 |
| | 1.0 mil FG @ 2.5 BUR/60 mil DG | | | | 2.0 mil FG @ 2.5 BUR/60 mil DG | | | |
| Motor Load (%) | 56.2 | 40.4 | 49.4 | 49.5 | 56.1 | 40.3 | 49.3 | 49.7 |
| E.S.O. (lb/HP-hr) | 10.02 | 13.91 | 11.23 | 11.44 | 9.98 | 13.93 | 11.27 | 11.42 |
| MD Modulus (psi) | 43,411 | 40,605 | 46,685 | 45,830 | 41,715 | 41,107 | 45,627 | 46,325 |
| TD Modulus (psi) | 53,857 | 54,827 | 57,202 | 55,091 | 46,621 | 62,189 | 57,493 | 55,489 |
| MD Tear (g/mil) | 38 | 63 | 76 | 110 | 68 | 98 | 141 | 159 |
| TD Tear (g/mil) | 653 | 622 | 695 | 595 | 513 | 433 | 466 | 441 |
| 26" Dart (g/mil) | 139 | 154 | 196 | 191 | 129 | 151 | 171 | 189 |
| Motor Load (—% Diff) | 0% | 28% | 12% | 12% | 0% | 28% | 12% | 11% |
| E.S.O. (% Diff) | 0% | 39% | 12% | 14% | 0% | 40% | 13% | 14% |
| MD Modulus (% Diff) | 0% | (−6%) | 8% | 6% | 0% | (−1%) | 9% | 11% |
| TD Modulus (% Diff) | 0% | 2% | 6% | 2% | 0% | 33% | 23% | 19% |
| MD Tear (% Diff) | 0% | 66% | 100% | 189% | 0% | 44% | 107% | 134% |
| TD Tear (% Diff) | 0% | (−5%) | 6% | (−9%) | 0% | (−16%) | (−9%) | (−14%) |
| 26" Dart (% Diff) | 0% | 11% | 41% | 37% | 0% | 17% | 33% | 47% |
| Average Mod (psi) | 48,634 | 47,716 | 51,944 | 50,461 | 44,168 | 51,648 | 51,560 | 50,907 |
| Cal. Dart per. '426 patent (g/mil) | 117 | 119 | 112 | 114 | 130 | 112 | 112 | 113 |
| Msrd. Dart vs. '426 (% diff.) | 119% | 129% | 175% | 168% | 99% | 135% | 152% | 167% |

TABLE 6

Further comparative film results from second pilot plant run

| | Exceed 1327CA UT00416- 073-241 | ML2610 PNX UT00416- 073-271 | LL3201.69 ZNC6 UT00416- 073-251 | Enable 2705CH UT00416- 073-222 | 2-6A UT00416- 073-181 |
|---|---|---|---|---|---|
| Density (g/cm3) | 0.928 | 0.928 | 0.927 | 0.928 | 0.926 |
| I-2 (dg/min) | 1.3 | 1.1 | 0.9 | 0.5 | 0.7 |
| MIR (I-21/I-2) | 15 | 20 | 25 | 45 | 27 |

TABLE 6-continued

Further comparative film results from second pilot plant run 1.0 mil FG @ 2.5 BUR/60 mil DG

|  |  |  |  |  |  |
|---|---|---|---|---|---|
| MD Modulus (psi) | 40,321 | 41,355 | 41,027 | 43,411 | 41,208 |
| TD Modulus (psi) | 46,204 | 47,206 | 49,793 | 53,857 | 49,406 |
| MD Tear (g/mil) | 154 | 173 | 136 | 38 | 280 |
| 26" Dart (g/mil) | 138 | 152 | 123 | 139 | 471 |

|  | Exceed 1327CA UT00416-073-242 | ML2610 PNX UT00416-073-272 | LL3201.69 ZNC6 UT00416-073-251 | Enable 2705CH UT00416-073-222 | 2-6A UT00416-073-182 |
|---|---|---|---|---|---|
| Density (g/cm3) | 0.928 | 0.928 | 0.927 | 0.928 | 0.926 |
| I-2 (dg/min) | 1.3 | 1.1 | 0.9 | 0.5 | 0.7 |
| MIR (I-21/I-2) | 15 | 20 | 25 | 45 | 27 |

2.0 mil FG @ 2.5 BUR/60 mil DG

|  |  |  |  |  |  |
|---|---|---|---|---|---|
| MD Modulus (psi) | 43,780 | 42,003 | 40,294 | 41,715 | 40,652 |
| TD Modulus (psi) | 47,366 | 48,004 | 49,340 | 46,621 | 51,075 |
| MD Tear (g/mil) | 160 | 197 | 226 | 68 | 214 |
| 26" Dart (g/mil) | 139 | 149 | 117 | 129 | 512 |

TABLE 7

Comparison of polymers formed in trim process with blends, all polymers use 1-butene comonomer

| Comonomer | | | | | | |
|---|---|---|---|---|---|---|
|  | C4/LD Blend C4 & LD | C4 BOCD C4 | C4 BOCD C4 | C4/LD Blend C4 & LD | C4 BOCD C4 | C4 BOCD C4 |

Polymer identification:

|  | C4-LLr Blend 80% LL 1001/ 20% LD071 | Catalyst System A: III/(IV-A, B) | Catalyst System B: III/(IV-A, B) | C4-LLr Blend 80% LL 1001/ 20% LD071 | Catalyst System A: III/(IV-A, B) | Catalyst System B: III/(IV-A, B) |
|---|---|---|---|---|---|---|
| Density (g/cm3) | 0.922 | 0.920 | 0.921 | 0.922 | 0.920 | 0.921 |
| I-2 (dg/min) | 0.8 | 1.0 | 0.8 | 0.8 | 1.0 | 0.8 |
| Melt Strength (cN) | 13 | 2.8 | 3.2 | 13 | 2.8 | 3.2 |
| MIR (I-21/I-2) | 28 | 37 | 38 | 28 | 37 | 38 |
| H2/C2 Ratio (ppm/m %) | Not applicable | 219.78 | 219.94 | Not applicable | 219.78 | 219.94 |
| C4/C2 Ratio (m/m) | Not applicable | 7.7 | 8.54 | Not applicable | 7.7 | 8.54 |
| Hf/Zr Mole Ratio | Not applicable | 1.16 | 1.52 | Not applicable | 1.16 | 1.52 |
| Motor Load (%) | 51 | 46 | 48 | 51 | 46 | 48 |
| E.S.O. (lb./HP-hr.) | 11.9 | 12.4 | 11.8 | 11.9 | 12.4 | 11.9 |
|  | 1.0 mil FG @ 2.5 BUR/60 mil DG | | | 2.0 mil FG @ 2.5 BUR/60 mil DG | | |
| MD Modulus (psi) | 37,491 | 25,564 | 25,133 | 30,597 | 28,424 | 25,228 |
| TD Modulus (psi) | 50,687 | 34,525 | 32,970 | 36,759 | 38,582 | 35,536 |
| MD Tensile (psi) | 6,266 | 6,472 | 5,475 | 5,149 | 5,331 | 4,406 |
| TD Tensile (psi) | 4,926 | 5,147 | 3,846 | 4,681 | 5,245 | 4,193 |
| Puncture - BE (in * lb./mil) | 14.1 | 17.6 | 21 | 14.6 | 17.5 | 11.6 |
| Total Haze (%) | 4.4 | 20.4 | 17.8 | 4.8 | 22.8 | 21.1 |
| Internal Haze (%) | 1.1 | 3.3 | 3.3 | 2.1 | 8.0 | 7.4 |
| MD Tear (g/mil) | 14 | 265 | 123 | 30 | 172 | 125 |
| TD Tear (g/mil) | 446 | 465 | 345 | 342 | 370 | 332 |
| 26" Dart (g/mil) | <50 | 134 | 90 | 93 | 213 | 146 |
| (log(Mw1) − log(Mw2))/(Tw1 − Tw2) | 0.0085 | −0.0188 | −0.0190 | | | |
| Mw1/Mw2 | 0.64 | 3.88 | 3.65 | | | |
| Tw1 − Tw2 (° C.) | −22.8 | −31.4 | −29.6 | | | |

TABLE 8

Further polymers formed in trim process with blends, all polymers use 1-butene comonomer

| | ZN C4 LLDPE | C4 BOCD | C4 BOCD | ZN C6 LLDPE |
|---|---|---|---|---|
| | | Comonomer | | |
| | C4 | C4 | C4 | C6 |
| | | Polymer identification: | | |
| | LL1001 x 26 | Part 120 Hf-P:EtInd 85:15 C4 80C | Part 130 Hf-P:EtInd 85:15 C4 86C | LL3001.63 |
| Density (g/cm3) | 0.921 | 0.921 | 0.921 | 0.919 |
| I-2 (dg/min) | 1.03 | 1.1 | 1 | 1.06 |
| Melt Strength (cN) | No data | No data | No data | No data |
| MIR (I-21/I-2) | 24 | 30 | 31 | 26 |
| H2/C2 Ratio (ppm/m %) | No data | 6.84 | 7.33 | No data |
| C4/C2 Ratio (m/m) | No data | 0.0654 | 0.0751 | Not applicable |
| Hf/R Mole Ratio | Not applicable | 1.18 | 1.23 | Not applicable |
| Motor Load (%) | 54 | 46 | 47 | 55 |
| E.S.O. (lb./HP-hr.) | 11.1 | 12.6 | 12.3 | 11.1 |
| | 1.0 mil FG @ 2.5 BUR/60 mil DG | | | |
| MD Modulus (psi) | 26,520 | 30,426 | 30,408 | 25,975 |
| TD Modulus (psi) | 31,159 | 40,725 | 41,893 | 30,127 |
| MD Tensile (psi) | 7,050 | 7,803 | 7,803 | 8,091 |
| TD Tensile (psi) | 4,779 | 6,452 | 6,401 | 7,123 |
| Puncture – BE (in * lb./mil) | 23.7 | 20.5 | 20.8 | 34.4 |
| Total Haze (%) | 5.7 | 30.9 | 31.5 | 6.5 |
| Internal Haze (%) | 2.0 | 3.8 | 4.1 | 2.6 |
| MD Tear (g/mil) | 139 | 234 | 264 | 436 |
| TD Tear (g/mil) | 463 | 474 | 501 | 747 |
| 26" Dart (g/mil) | 98 | 208 | 197 | 159 |
| (log(Mw1) – log(Mw2))/(Tw1 – Tw2) | 0.0078 | –0.0148 | –0.0132 | 0.0082 |
| Mw1/Mw2 | 0.60 | 2.62 | 2.41 | 0.51 |
| Tw1 – Tw2 (o C) | –28.1 | –28.3 | –28.8 | –36.0 |

TABLE 9

Summary of Cryo-CFC Analysis with Equal Halves

Control Polymers (Commercial Samples)

| Polymer Identification | A | B | C | D | E | F | G | H |
|---|---|---|---|---|---|---|---|---|
| Description | LL3001 | Dowlex 2045 | Exceed 1018CA | Enable 2010 | Borstar FB2230 | Evolve SP3010 | Elite 5400 | Eltex PF6212 |
| (log(Mw1) – log(Mw2))/(Tw1 – Tw2) | 0.0084 | 0.0142 | –0.0012 | 0.0179 | 0.0037 | 0.0018 | –0.0085 | –0.0001 |
| Mw1/Mw2 | 0.48 | 0.49 | 1.04 | 0.76 | 0.72 | 0.89 | 1.59 | 1.00 |
| Tw1 – Tw2 (° C.) | –37.6 | –21.6 | –14.5 | –6.7 | –37.9 | –28.1 | –23.8 | –18.2 |

Experimental Polymers

| Polymer Identification (Table 1) | 1-10 | 1-1 | 1-2 | 1-4 | 1-3 | 1-5 | 1-6 | 1-7 |
|---|---|---|---|---|---|---|---|---|
| (log(Mw1) – log(Mw2))/(Tw1 – Tw2) | –0.0155 | –0.0197 | –0.0191 | –0.0213 | –0.0210 | –0.0149 | –0.0131 | –0.0144 |
| Mw1/Mw2 | 2.65 | 2.88 | 3.91 | 3.36 | 3.45 | 2.52 | 2.67 | 2.82 |
| Tw1 – Tw2 (deg. C.) | –27.3 | –23.3 | –31.0 | –24.7 | –25.6 | –26.8 | –32.6 | –31.2 |

General Procedures for Forming Catalyst Components

All manipulations were performed in an $N_2$ purged glovebox or using standard Schlenk techniques. All anhydrous solvents were purchased from Sigma-Aldrich and were degassed and dried over calcined $Al_2O_3$ beads prior to use. Toluene for the catalyst preparations was pre-dried with $Al_2O_3$ beads then dried over SMAO 757 before use. Deuterated solvents were purchased from Cambridge Isotope Laboratories and were degassed and dried over alumina beads prior to use. Reagents used were purchased from Sigma-Aldrich, with the exception of $ZrCl_4$ 99+% which was purchased from Strem Chemicals, bis(n-propyl-cyclopentadienyl)zirconium dimethyl ($HfPMe_2$) was purchased from Boulder Scientific and meso-O—$(SiMe_2Indenyl)_2$ $ZrCl_2$ (V-A) was purchased from Süd-Chemie Catalytica. $^1H$ NMR measurements were recorded on a 250 Mz or 500 Mz Bruker spectrometer.

Indenyllithium 50.43 g (434.14 mmol) of freshly distilled indene was dissolved in 1 L of pentane and ca. 25 mL of $Et_2O$ was added. 268.47 mL (429.55 mmol) of 1.6M n-butyllithium in hexanes was added to the clear stirring solution over a span of 5 minutes. Upon addition of the n-butyllithium a white solid precipitated and the supernatant took on a light yellow color. After stirring overnight the suspension was filtered and the white solid dried in vacuo. 46.51 g (380.95 mmol) of product was recovered for an 88.7% yield. $^1H$ NMR (THF-$d_8$): δ 5.91 (2H, d), 6.44 (2H, m), 6.51 (1H, t), 7.31 (2H, m).

Indenyllithium, Procedure II

Freshly distilled indene (50.43 g, 434.1 mmol) was dissolved in 1 L of pentane. $Et_2O$ (25 mL) then 1.6M n-butyllithium in hexanes (268.5 mL, 429.6 mmol) were added to the clear stirring solution over a span of 5 min. A white solid precipitated and the supernatant took on a light yellow color. After stirring overnight the suspension was filtered then dried in vacuo to yield a white solid (46.51 g, 381.0 mmol, 88.7%). $^1H$ NMR (THF-$d_8$): δ 5.91 (d, 2H), 6.44 (m, 2H), 6.51 (t, 1H), 7.31 (m, 2H).

1-Ethylindene 46.51 g (380.95 mmol) of indenyllithium was dissolved in 250 mL of $Et_2O$, and a separate solution was made of 95.94 g (615.12 mmol) of ethyliodide in 400 mL of $Et_2O$. The ethyliodide solution was cooled to −30° C. in and the indenyllithium solution was cooled to 0-10° C. using a dry ice/acetone bath. The indenyllithium was added to the clear stirring solution of ethylidode via cannula transfer. The solution became a light yellow to yellow color upon addition of the indenyllithium solution. The reaction was allowed to stir overnight and slowly warm to room temperature. After stirring overnight the flask was brought into the box and the $Et_2O$ was reduced in vacuo. Once LiI began to precipitate, 300 mL of pentane was added and the white suspension was filtered resulting in a light orange solution. The pentane was evaporated where more LiI precipitated and a light orange oily liquid was obtained. The crude product was distilled under diminished pressure using a rotary vacuum pump to a slight yellow clear liquid. $^1H$ NMR showed~90% 1-Ethylindene and ~10% 3-Ethylindene. Possible isomerization could have occurred due to a small amount of acid present during the distillation as none was present in the crude $^1H$ NMR spectrum. 44.27 g (306.96 mmol) of product was isolated for an 80.6% yield. $^1H$ NMR ($CD^2Cl^2$): δ 0.96 (3H, t), 1.59 (1H, q), 1.99 (1H, q), 3.41 (1H, m), 6.58 (1H, d), 6.59 (1H, d), 7.24 (2H, m), 7.41 (2H, dd).

1-Ethyl indenyllithium 44.27 g (306.98 mmol) of 1-Ethylindene containing ~10% 3-Ethylindene was dissolved in 500 mL of pentane and ca. 3 mL of $Et_2O$. To the clear stirring solution was added 188.28 mL (301.25 mmol) of 1.6M n-butyllithium in hexanes over 10 minutes. Immediately a flaky white precipitate formed and caused the stirring stop. The mixture was manually stirred to ensure proper incorporation of reagents and the suspension was allowed to sit overnight. The suspension was filtered and the white solid dried in vacuo. 43.27 g (288.18 mmol) of product was obtained for a 95.7% yield. 1H NMR (THF-d8): δ 1.26 (3H, triplet), 2.86 (2H, quartet), 5.72 (doublet, 1H), 6.38 (dd 1H), 6.43 (2H, m), 7.26 (1H, t), 7.30 (1H, m).

Rac and meso-bis(1-Ethyl-indenyl)zirconium dimethyl (1-EtInd)$_2$ZrMe$_2$, formulas (IV-A) and (IV-B)

7.00 g (46.65 mmol) of 1-Ethyl-indenyllithium was dissolved in 74 mL of 1, 2-dimethoxyethane (DME) and a separate solution was made with 5.43 g (23.30 mmol) of $ZrCl_4$ in 75 mL of DME. To the clear $ZrCl_4$ solution was added the bright yellow solution of 1-ethyl-indenyllithium via pipette over a fifteen minute period. Upon initial addition the solution took on a yellow color, and after five minutes into the addition a precipitate formed and an orange-yellow color ensued. Ten minutes into the addition the supernatant turned orange with a yellow precipitate, and once all the 1-ethyl-indenylltihium solution was added the mixture turned back to yellow. The reaction was allowed to stir overnight.

A crude $^1H$ NMR spectrum of the slurry showed a rac/meso ratio of ~1.1:1; however this can be misleading since the rac isomer is more soluble in DME than the meso isomer. Regardless of the isomer ratio, 15.61 mL (46.83 mmol) of 3.0M $CH_3MgBr$ in $Et_2O$ was added in 1 mL portions over ten minutes. After the tenth addition the yellow mixture turned an orange color. Upon the final addition of the Grignard reagent, the mixture had turned brown and the reaction was allowed to stir overnight. A $^1H$ NMR spectrum of the crude mixture revealed a 1.1:1 meso/rac ratio. The DME was evaporated and the brown solid was extracted with 3×20 mL of toluene plus an additional 10 mL. The light brown solid obtained after solvent removal was washed with 10 mL of pentane and dried in vacuo. 8.26 g (20.26 mmol) of the off-white solid was obtained for an 87% yield. Dichloride spectral data: $^1H$ NMR ($CD_2Cl_2$): δ 1.16 (6.34H, t, rac), 1.24 (6H, t, meso), 2.73-2.97 (8H, overlapping q), 5.69 (1.82H, dd, meso), 5.94 (1.92H, dd, rac), 6.06 (1.99H, d, rac), 6.35 (1.84H, d, meso), 7.22-7.65 (16H, m). Dimethyl Spectral Data: $^1H$ NMR ($C_6D_6$): δ −1.40 (3.33H, s, meso), −0.895 (6H, s, rac), −0.323 (3.34H, s, meso), 1.07 (13H, overlapping t), 2.47 (4H, overlapping q), 2.72 (4H, q), 5.45-5.52 (8H, m), 6.91 (8H, m), 7.06-7.13 (4H, m), 7.30 (4H, m).

75% HfPMe$_2$/25% (1-EtInd)$_2$ZrMe$_2$ Catalyst Preparation Batch 1

An 8 L Morton flask was charged with 375 g of SMAO then 2 L of pentane was added. The mixture clumped up which made stirring difficult so another 2 L of pentane was added followed by an addition 375 g of SMAO. The mechanical stirrer was set ca. 140 rpm. Two separate solutions were made with 2.89 g (7.09 mmol) of (1-EtInd)

$_2$ZrMe$_2$ and 8.86 g (20.95 mmol) of HfPMe$_2$ in 20 mL of toluene. The separate solutions were added to a roundbottom flask and an additional 160 mL of toluene was added and the solution was allowed to stir for ca. 20 minutes. The solution was added to the slurry of SMAO in pentane with an additional funnel drop wise over the course of an hour. The mixture turned a green color upon addition of the mixed metallocene solution and was allowed to stir for an additional hour. The mixture was then filtered batch wise and dried in vacuo for a total of 8 hours. It is important to note that ca. 7 Al$_2$O$_3$ beads were present from the pentane and trace red solids were also present during the preparation. The Al$_2$O$_3$ beads were removed by hand during filtration and by sifting the final product.

75% HfPMe$_2$/25% (1-EtInd)$_2$ZrMe$_2$ Catalyst Preparation Batch 2

A similar procedure as described above was employed for the second batch of 75/25 catalyst. A mixture of SMAO was used comprising of 204.15 g from a first run, 176.17 g from a second run, 209.49 g from a third run, and 160.19 g from a fourth run. For the second batch, 4 L of pentane was added first to the Morton flask followed by the SMAO so clumping would not occur. Two separate solutions were made with 2.87 g (7.09 mmol) of (1-EtInd)$_2$ZrMe$_2$ and 8.94 g (20.95 mmol) of HfPMe2 in 20 mL of toluene.

50% HfPMe$_2$/50% (1-EtInd)$_2$ZrMe$_2$ Catalyst Preparation Batch 1 & 2

The same procedure used to prepare the second batch of 75/25 catalyst was used for both sets of 50/50 catalyst. Batch 1 used SMAO from the fourth run, 5.75 g (14.10 mmol) of (1-EtInd)$_2$ZrMe$_2$, and 5.97 g (14.11 mmol) of HfPMe$_2$. Batch 2 used SMAO from a fifth run, 5.75 g (14.09 mmol) of (1-EtInd)$_2$ZrMe$_2$, and 5.97 g (14.11 mmol) of HfPMe$_2$.

2,3,4,5-tetramethyl-1-trimethylsilyl-cyclopenta-2,4-diene

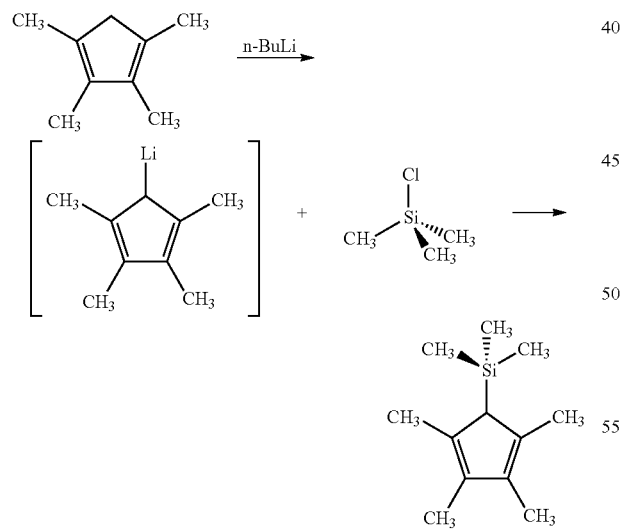

To a 2 liter Erlenmeyer flask, dissolved yellow oil of tetramethylcyclopentadiene (50 g, 409 mmol—obtained from Boulder Scientific) in 1 liter of anhydrous THF. Stirred at room temperature as n-butyllithium (175 ml, 437 mmol) added through a 60 ml plastic syringe with a 20 gauge needle regulating dropwise flow. Formation of a pale yellow precipitate was observed. Reaction is a yellow slurry upon complete addition of lithium reagent. Stirred 1 hr at room temperature, then with vigorous stirring chlorotrimethylsilane (60 ml, 470 mmol) was added and reaction allowed to stir overnight at room temperature. After stirring at room temperature for 15 hr, mixture is a yellow solution. Removed THF solvent with under a stream of N$_2$ to afford an oily residue, which was then extracted with 1 liter of dry pentane and filtered through a celite pad on coarse frit. Removed volatiles under vacuum to afford product as a yellow oil: 62.9 g, 79%. $^1$H NMR (C$_6$D$_6$, 250 MHz): δ −0.04 (s, Si(CH$_3$)$_3$), δ 1.81, (s, CH$_3$), δ 1.90 (s, CH$_3$), δ 2.67 (s, CH)

(Tetramethylcyclopentadienyl)zirconium trichloride

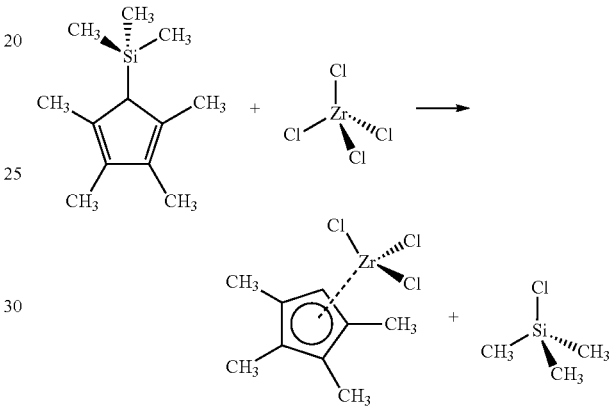

In a drybox, charged solid ZrCl$_4$ (30.0 g, 129 mmol) to a 450 ml Chemglass pressure vessel with magnetic spinbar, suspended in 100 ml dry toluene. Dispensed 2,3,4,5-tetramethyl-1-trimethylsilyl-cyclopenta-2,4-diene as a yellow oil (27.5 g, 142 mmol) and rinsed down with additional 100 ml dry toluene. Sealed pressure vessel with threaded cap with Viton o-ring, and heated on a fitted aluminum heating mantle to 110° C. for 90 min. Solution darkens with time, and insolubles were present during reaction. Vessel was allowed to stir overnight and cool to room temperature. Vessel was opened and solvent volume reduced under stream of N$_2$, affording a thick red sludge. Extracted with 2×50 ml dry pentane then with 100 ml dry ether. Red solution removed and recovered product as pale red solid: 35.4 g, 85%. $^1$H NMR (C$_6$D$_6$, 250 MHz): δ 1.89 (br s, CH$_3$), δ 2.05 (br s, CH$_3$), δ 5.78 (br s, CH)

1-Methyl-indenyllithium

Freshly distilled 3-Methylindene (33.75 g 259.24 mmol) was dissolved in pentane (1 L). Et2O (10 ml), then 1.6M n-butyllithium in hexanes (107 mL, 171.2 mmol) and 2.5M n-butyllithium in hexanes (34.2 mL, 85.5 mmol) were added to the clear stirring solution. Immediately a flaky white solid precipitated. After stirring overnight, the suspension was filtered and the white solid dried in vacuo (33.88 g, 248.90 mmol, 97%). 1H NMR (THF-d8): δ 2.41 (s, 3H), 5.68 (d, 1H), 6.31 (d, 1H), 6.41 (m, 2H), 7.22 (m, 2H).

1,3-dimethylindene

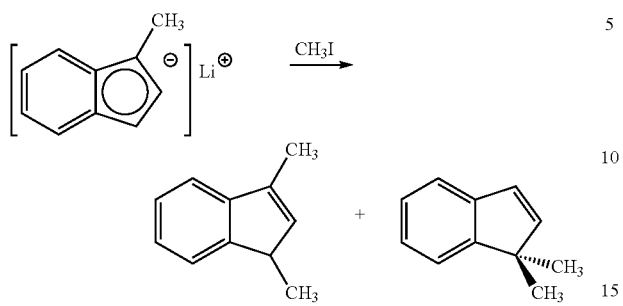

In a drybox, iodomethane (2.0 ml, 32.1 mmol) was dissolved in 80 ml dry diethyl ether in a 250 ml round bottom flask with magnetic spinbar. Flask was placed in an isohexane cold bath (−25° C.) in a wide mouth dewar. In a separate 100 ml Erlenmeyer flask, a room temperature solution of 1-methylindenyl lithium (3.50 g, 25.7 mmol) was prepared in 50 ml dry diethyl ether, affording a yellow solution. Slow, dropwise addition of indenyl lithium solution to the cold, stirred solution of iodomethane was performed over 15 min. Continued stirring at low temperature for 30 min, then removed the cold bath and allowed the reaction to warm to room temperature overnight. Solution is turbid white after stirring 15 hr at room temperature. Reduced solution volume under nitrogen flow, then volatiles evaporated under high vacuum. Extracted solids with 2×80 ml isohexane and filtered through pad of celite on coarse frit. Filtrates evaporated under high vacuum to afford brown oil. Dissolved in 5 ml dichloromethane and loaded via pipet onto silica gel column (Biotage SNAP 100 g), eluting with dichloromethane:isohexane (gradient, 2-20%). Fractions combined and evaporated to afford a clear oil. Collected 2.54 g, 68%. $^1$H NMR (C$_6$D$_6$, 500 MHz): δ 1.11 (d, J=7.5 Hz, —CHCH$_3$), δ 1.96 (s, CH═CCH$_3$), δ 3.22 (m, CHCH$_3$), δ 5.91 (m, CH═CCH$_3$), δ 7.15-7.27 (aromatic CH). Mixture contains minor isomer 3,3-dimethylindene in 1:10 ratio with desired product. δ 1.17 (s, CH$_3$), δ 6.14 (d, J=5.5 Hz, CHH), δ 6.51 (d, J=5.5 Hz, CHH).

1,3-dimethylindenyl lithium

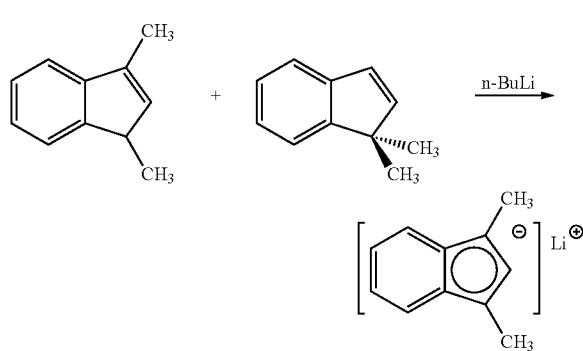

Dissolved 2.54 g (17.6 mmol) of clear oil, 10:1 mixture of 1,3-dimethylindene and 3,3-dimethylindene, in 35 ml dry pentane. Stirred at room temperature as 6.2 ml of a 2.5 M hexane solution of n-butyllithium (15.5 mmol) was added slowly, dropwise. White precipitate formed immediately. Stirred at room temperature for 45 min, then filtered supernatant via cannula. Suspended the residue in 30 ml dry pentane and cooled in drybox freezer (−27° C.) for 60 min. Filtered supernatant and dried in vacuo to white powder, 2.34 g (88%) and used as-is for subsequent reaction step without characterization.

[(1,3-dimethylindenyl)(tetramethylcyclopentadienyl)]Zirconium dichloride, formula (IV-D)

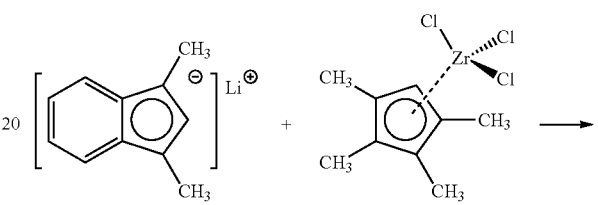

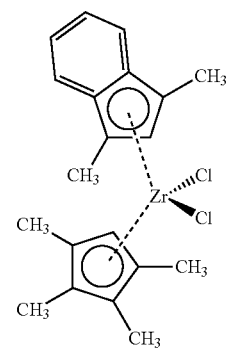

Weighed 3.50 g (10.98 mmol) tan powder of (tetramethylcyclopentadienyl)zirconium trichloride into a 100 ml flat bottom glass bottle with magnetic spinbar. Suspended in 80 ml dry diethyl ether. Stirred as 1,3-dimethylindenyl lithium (1.65 g, 10.99 mmol) added as powder over several minutes. Rinsed down with additional 20 ml ether. Capped bottle and stirred overnight at room temperature. Mixture a yellow slurry after stirring 15 hr at room temperature. Evaporated volatiles under high vacuum, then extracted residue with 2×80 ml dichloromethane. Filtered through celite pad on coarse frit. Concentrated in vacuo and filtered again through fresh celite on coarse frit. Dried in vacuo to free flowing yellow powder, 3.6 g (77%). $^1$H NMR (CD$_2$Cl$_2$, 500 MHz): δ 1.89 (s, CH$_3$ of Cp$^{Me4}$), δ 1.90 (s, CH$_3$ of Cp$^{Me4}$), δ 2.40 (s, CH$_3$ of C$_9$ fragment), δ 5.67 (s, CH of Cp$^{Me4}$), δ 6.33 (s, CH of C$_9$ fragment), δ 7.24 (AA'BB', aromatic CH of C$_9$ fragment), δ 7.52 (AA'BB', aromatic CH of C$_9$ fragment). Contains ca. 15% diethyl ether.

[(1,3-dimethylindenyl)(tetramethylcyclopentadienyl)]Zirconium dimethyl, formula (IV-D)

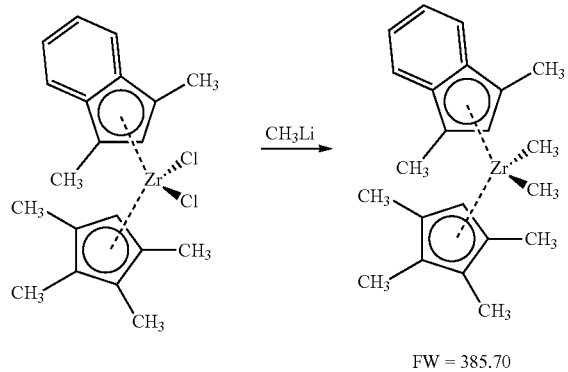

FW = 385.70

In the drybox, suspended bright yellow powder of (1,3-Me$_2$Ind)(Cp$^{Me4}$)ZrCl$_2$ (3.6 g, 8.4 mmol) in 75 ml dry diethyl ether in a 100 ml amber glass flat-bottom bottle with magnetic spinbar. Cooled bottle to −10 C in isohexane bath, stirred as solution of methyllithium (1.6 M in ether) delivered via syringe in portions (4×3 ml, 19.2 mmol). Capped bottle with septum and stirred overnight, allowing cold bath to slowly warm to room temperature. Evaporated slurry to dryness under high vacuum. Extracted with 3×50 ml dichloromethane and filtered through celite on coarse frit. Concentrated under stream of nitrogen, then added pentane. Stirred 15 min then evaporated volatiles. Washed solids with cold pentane, dried in vacuo. Collected as tan powder, 1.67 g; second crop recovered from filtrate, 0.52 g. Combined yields 2.19 g, 67%. $^1$H NMR (CD$_2$Cl$_2$, 500 MHz): δ −1.22 (s, ZrCH$_3$), 1.78 (s, CH$_3$ of Cp$^{Me4}$ fragment), 1.87 (s, CH$_3$ of Cp$^{Me4}$ fragment), 2.25 (s, CH$_3$ of C$_9$ fragment), 4.92 (s, CH of Cp$^{Me4}$ fragment), 5.60 (s, CH of C$_9$ fragment), 7.14 (AA'BB', aromatic CH of C$_9$ fragment), 7.44 (AA'BB', aromatic CH of C$_9$ fragment). $^{13}$C{$^1$H} NMR (CD$_2$Cl$_2$, 125 MHz): δ 11.64 (CH$_3$ of Cp$^{Me4}$ fragment), 12.91 (CH$_3$ of C$_9$ fragment), 13.25 (CH$_3$ of Cp$^{Me4}$ fragment), 37.23 (ZrCH$_3$), 106.34 (CH of Cp$^{Me4}$ fragment), 115.55 (CH of C$_9$ fragment); quaternary $^{13}$C resonances 107.36, 117.51, 122.69, and 125.06.

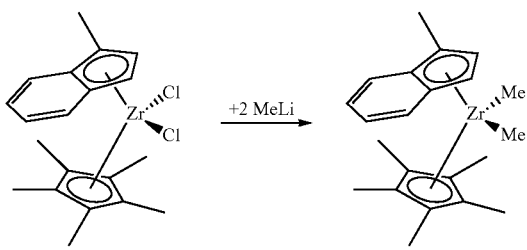

(1-Methylindenyl)(pentamethylcyclopentadienyl)zirconium(IV)dichloride, chloride version of formula (IV-C)

In the drybox, weighed 1-Methyl-1H-indene oil (1.85 g, 14.2 mmol) into a 250 ml roundbottom flask and dissolved in 25 ml dry diethyl ether. Added n-Butyllithium (1.6 M in hexanes, 12.0 ml, 19.2 mmol) dropwise from a 20 ml needle/syringe to form a yellow solution. Stirred at room temperature for 60 minutes. To the yellow-orange solution of (1-methyl)indenyllithium was added Cp*ZrCl$_3$ (4.51 g, 13.5 mmol, used as received from Aldrich-475181) quickly in one portion as a yellow crystalline solid. Stirred the yellow-orange slurry overnight at room temperature. The mixture was allowed to settle for 30 min. Dark brown solution was decanted from pale yellow solids, rinsed solids on glass frit with 100 ml dry ether. Extracted solids on frit with 100 ml dichloromethane, affording a yellow suspension. Filtered through Celite plug on frit and evaporated volatiles to yield a yellow solid. Recrystallized from ether/pentane to afford 2.70 g (47%). Additional material obtained from mother liquor: 1.19 g (20%) $^1$H NMR (C$_6$D$_6$, 500 MHz, 35° C.): δ 1.70 (15H, s, Cp*), δ 2.30 (3H, s, indenyl CH$_3$), δ 5.56 (2H, ABq, indenyl CH, CH), δ 7.05 (1H, dd, indenyl CH), δ 7.10 (1H, dd, indenyl CH), δ 7.24 (1H, dt, indenyl CH), δ 7.56 (1H, dq, indenyl CH).

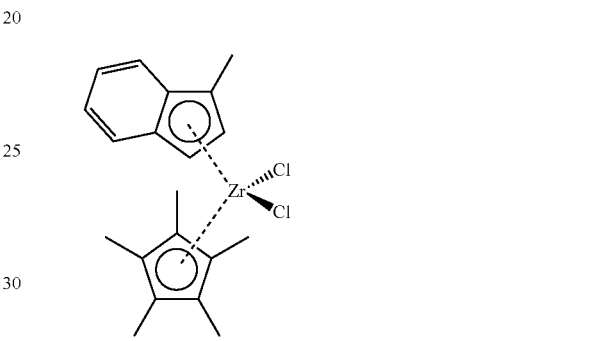

(1-Methylindenyl)(pentamethyicyclopentadienyl)zirconium(IV)dimethyl, formula (IV-C)

(1-Methylindenyl)(pentamethylcyclopentadienyl)zirconiumdichloride (4.92 g, 11.5 mmol) was slurried in 50 mL diethyl ether and cooled to −50° C. To this, a solution of MeLi (14.8 mL of a 1.71M solution in diethyl ether, 25.4 mmol) was added slowly by syringe. The mixture was left to stir and slowly warm to room temperature to give a pink slurry. After 16 h, the solvent was removed under vacuum and the residue extracted with toluene. The insolubles were removed by filtering through a frit lined with Celite and the solvent was removed to give an orange oily solid. The solid was washed with pentane and dried under vacuum (3.89 g, 88% yield). $^1$H NMR δ (C$_6$D$_6$): 7.53 (d, 1H, 8-IndH), 7.13-6.99 (m, 3H, 5,6,7-IndH), 5.21 (d, 1H, 2-IndH), 5.11 (d, 1H, 3-IndH), 2.20 (s, 3H, 1-MeInd), 1.69 (s, 15H, CpMe$_5$), −0.51 (s, 3H, ZrMe), −1.45 (s, 3H, ZrMe).

Preparation of meso-O—(SiMe$_2$Indenyl)$_2$ZrMe$_2$

Meso-O—(SiMe$_2$Indenyl)$_2$ZrCl$_2$ (21.2 g; 40.6 mmol) was slurried in diethyl ether (ca. 250 mL) and MeMgBr (28.4 mL; 3.0 M in diethyl ether; 85.2 mmol) was added with stirring. After stirring at room temperature for 2 h, the ether was removed under vacuum and the resulting solid was extracted with heptane (250 mL at 80° C.) then filtered. After cooling to −35° C. overnight, the yellow crystalline solid was isolated by filtration then washed with pentane and dried under vacuum; yield=13 g. $^1$H NMR δ (C$_6$D$_6$): 7.54 (m, 2H); 7.40 (m, 2H); 7.00 (m, 2H); 6.93 (m, 2H); 6.31 (m, 2H); 5.82 (m, 2H); 0.44 (s, 6H); 0.33 (s, 6H); −0.02 (s, 3H); −2.08 (s, 3H).

Dehydration of Silica at 610° C.

Ineos ES757 silica (3969 g) was charged into a dehydrator (6 ft length, 6.25 in diameter) equipped with a 3-zone heater then fluidized with dry N2 gas at a flow rate of 0.12 ft³/s. Afterwards, the temperature was raised to 200° C. in a 2 h period. After holding at 200° C. for 2 h, the temperature was raised to 610° C. in a 6 h period. After holding at 610° C. for 4 h, the temperature was allowed to cool to ambient temperature over a 12 h period. The silica was transferred under $N_2$ to an APC can, and then stored under $N_2$ pressure (20 psig).

Preparation of Methyl Aluminoxane Supported on Silica (SMAO).

In a typical procedure, Ineos ES757 silica (741 g), dehydrated at 610° C., was added to a stirred (overhead mechanical conical stirrer) mixture of toluene (2 L) and 30 wt % solution of methyl aluminoxane in toluene (874 g, 4.52 mol). The silica was chased with toluene (200 mL) then the mixture was heated to 90° C. for 3 h. Afterwards, volatiles were removed by application of vacuum and mild heat (40° C.) overnight then the solid was allowed to cool to room temperature.

Typical Large Scale Catalyst Preparations for R124 Pilot Plant Testing

A 5 L 3-neck Morton flask was charged with pentane (4 L) then stirred (140 rpm) with a mechanical stirrer while charged with SMAO (375 g). A solution containing $(1\text{-EtInd})_2\text{ZrMe}_2$, $\text{HfPMe}_2$, and toluene was added with an addition funnel over the course of an hour. The slurry took on a green color and was allowed to stir for an additional hour. The mixture was then filtered and dried in vacuo for a total of 8 hours.

Mixing of the Catalysts

TABLE 10

Catalyst mixtures tested

| Catalyst Mixture | (1EtInd)2ZrMe2 mass (g) | mmol | (CpPr)2HfMe2 mass (g) | mmol | (1EtInd)2ZrMe2 mole fraction |
|---|---|---|---|---|---|
| 1 (75/25) | 2.89 | 7.09 | 8.86 | 20.95 | 0.25 |
| 2 (75/25) | 2.87 | 7.04 | 8.94 | 21.14 | 0.25 |
| 3 (50/50) | 5.75 | 14.10 | 5.97 | 14.12 | 0.50 |
| 4 (50/50) | 5.75 | 14.10 | 5.97 | 14.12 | 0.50 |

The two 75/25 batches were combined in a 4 L Nalgene bottle and manually mixed by spinning and shaking the bottle. The two 50/50 batches were also mixed in the same manner. Trim solutions were made by dissolving the catalyst dimethyl complex in dry and degassed isopentane to form a solution of 0.015 to 0.02 weight percent.

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A polymer, comprising ethylene and at least one alpha olefin having from 4 to 20 carbon atoms, wherein the polymer has:
    a melt index ratio (MIR) greater than about 40;
    a value for Mw1/Mw2 of at least about 2.0, wherein Mw1/Mw2 is a ratio of a weight average molecular weight (Mw) for a first half of a temperature rising elution (TREF) curve from a cross-fraction (CFC) analysis to a Mw for a second half of the TREF curve; and
    a value for Tw1−Tw2 of less than about −15° C., wherein Tw1−Tw2 is a difference of a weight average elution temperature (Tw) for the first half of the TREF curve to a Tw for the second half of the TREF curve.

2. The polymer of claim 1, wherein the polymer has:
    an average modulus of greater than about 20,000 psi at 1 mil film gauge; and
    a dart impact strength of greater than about 100 g/mil at 1 mil film gauge.

3. The polymer of claim 1, wherein the polymer has no negative inflection point in a van Gurp Palmen (vGP) plot at a frequency of between about 0.1 rad/s and 300 rad/s at 190° C.

4. The polymer of claim 1, wherein the polymer has a relationship between average modulus (M) and dart impact strength in g/mil (DIS) complying with the formula:

$$\text{DIS} \geq 0.8 \times [100 + e^{(11.71 - 0.000268 \times M + 2.183 \times 10^{-9} \times M^2)}].$$

5. The polymer of claim 1, comprising:
    a lower molecular weight polymer formed by a first catalyst and a higher molecular weight polymer formed by a second catalyst, wherein:
    the lower molecular weight polymer has a density of about 0.02 greater than the density of the higher molecular weight polymer; and
    the mol ratio of the first catalyst to the second catalyst is between about 1:1 and 1:10.

6. The polymer of claim 5, wherein the lower molecular weight polymer has a peak molecular weight of less than about ¼ of the peak molecular weight of the higher molecular weight polymer.

7. The polymer of claim 1, comprising a polymer chain formed by a catalyst system comprising bis(n-propylcyclopentadienyl) hafnium $(CH_3)_2$.

8. The polymer of claim 1, comprising a polymer chain formed by a catalyst system comprising bis(n-butyl, methyl cyclopentadienyl) zirconium $(CH_3)_2$.

9. The polymer of claim 1, comprising a polymer chain formed by a catalyst system comprising bis(1-ethylindenyl) zirconium $(CH_3)_2$.

10. The polymer of claim 1, comprising a polymer chain formed by a catalyst system comprising any one of the compounds represented by the following formulas:

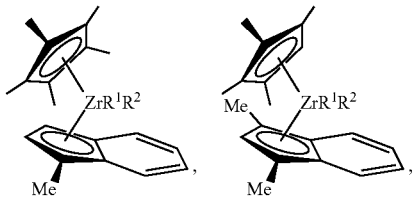

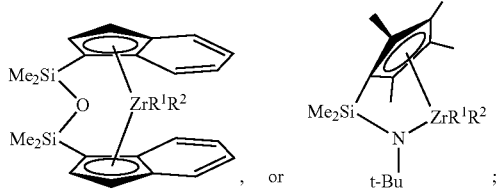

wherein R$^1$ and R$^2$ are each, independently, methyl, chloro, fluoro, or a hydrocarbyl group.

11. The polymer of claim 1, comprising polymer chains formed by a catalyst system comprising bis(n-propylcyclopentadienyl) hafnium (CH$_3$)$_2$ and bis(1-ethylindenyl) zirconium (CH$_3$)$_2$.

12. The polymer of claim 1, comprising polymer chains formed by a catalyst system comprising bis(n-propylcyclopentadienyl) hafnium (CH$_3$)$_2$ and meso-O(SiMe$_2$Ind)$_2$ZrMe$_2$.

13. The polymer of claim 1, comprising polymer chains formed by a catalyst system comprising a compound represented by one of the following formulas:

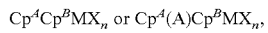

Cp$^A$Cp$^B$MX$_n$ or Cp$^A$(A)Cp$^B$MX$_n$, wherein M is a Group 4, 5, or 6 atom; Cp$^A$ and Cp$^B$ are each bound to M and are independently selected from the group consisting of cyclopentadienyl ligands, substituted cyclopentadienyl ligands, ligands isolobal to cyclopentadienyl and substituted ligands isolobal to cyclopentadienyl; (A) is a divalent bridging group bound to both Cp$^A$ and Cp$^B$ selected from the group consisting of divalent C$_1$ to C$_{20}$ hydrocarbyls and C$_1$ to C$_{20}$ heteroatom containing hydrocarbonyls, wherein the heteroatom containing hydrocarbonyls comprise from one to three heteroatoms; X is a leaving group selected from the group consisting of chloride ions, bromide ions, C$_1$ to C$_{10}$ alkyls, and C$_2$ to C$_{12}$ alkenyls, carboxylates, acetylacetonates, and alkoxides; and n is an integer from 1 to 3.

14. A polymer, comprising ethylene and at least one alpha olefin having 4 carbon atoms, wherein the polymer has:
   a total haze of less than about 30% at 1 mil film gauge;
   an average modulus of greater than about 30,000 psi at 1 mil film gauge;
   a dart impact strength of greater than about 120 g for a 1 mil film;
   a melt index ratio (MIR) greater than about 25; and
   an Elmendorf machine direction tear of greater than about 170 g at 1 mil film gauge.

15. The polymer of claim 14, wherein the polymer has a relationship between average modulus (M) and dart impact strength in g/mil (DIS) complying with the formula:

$$DIS \geq 0.8 \times [100 + e^{(11.71 - 0.000268 \times M + 2.183 \times 10^{-9} \times M^2)}].$$

16. The polymer of claim 14, comprising a polymer chain formed by a catalyst system comprising any one of the compounds represented by the following formulas:

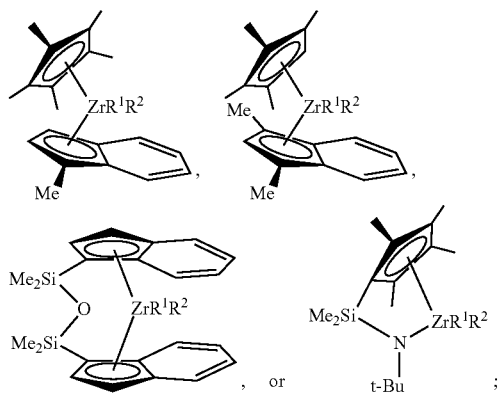

wherein R$^1$ and R$^2$ are each, independently, methyl, chloro, fluoro, or a hydrocarbyl group.

17. A polymer, comprising ethylene and at least one alpha olefin having 4 carbon atoms, wherein the polymer has:
   a value for melt index ratio (MIR) of between about 25 and about 35;
   a value for Mw1/Mw2 of at least about 2.0, wherein Mw1/Mw2 is a ratio of a weight average molecular weight (Mw) for a first half of a temperature rising elution (TREF) curve to a Mw for a second half of the TREF curve; and
   a value for Tw1−Tw2 of less than about −15° C., wherein Tw1−Tw2 is a difference of a weight average elution temperature (Tw) for the first half of the TREF curve to a Tw for the second half of the TREF curve.

* * * * *